(12) United States Patent
Takada

(10) Patent No.: US 9,314,378 B2
(45) Date of Patent: Apr. 19, 2016

(54) METHOD AND APPARATUS FOR MANUFACTURING ADHESIVE PATCH

(75) Inventor: Kiyotaka Takada, Tosu (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 13/501,764

(22) PCT Filed: Sep. 30, 2010

(86) PCT No.: PCT/JP2010/067129
§ 371 (c)(1),
(2), (4) Date: May 31, 2012

(87) PCT Pub. No.: WO2011/046023
PCT Pub. Date: Apr. 21, 2011

(65) Prior Publication Data
US 2012/0234484 A1 Sep. 20, 2012

(30) Foreign Application Priority Data

Oct. 14, 2009 (JP) ............................... P2009-237571
Nov. 16, 2009 (JP) ............................... P2009-261314
Jun. 11, 2010 (JP) ............................... P2010-134407

(51) Int. Cl.
*B32B 38/04* (2006.01)
*B32B 37/06* (2006.01)
(Continued)

(52) U.S. Cl.
CPC ......... *A61F 13/0289* (2013.01); *A61F 13/0008* (2013.01); *A61F 13/00085* (2013.01);
(Continued)

(58) Field of Classification Search
CPC .................... A61F 13/0259; A61F 13/0289
USPC ........................................................ 156/212
See application file for complete search history.

(56) References Cited

U.S. PATENT DOCUMENTS 2,233,209 A    2/1941    Herzog
2,280,506 A    4/1942    Betts
(Continued)

FOREIGN PATENT DOCUMENTS

CA    2348854      6/2000
CN    1333672 S    1/2002
(Continued)

OTHER PUBLICATIONS

International Preliminary Report on Patentability for PCT Application No. JP2010/067140; 5 pages; mailed on May 24, 2012.
(Continued)

*Primary Examiner* — Michael N Orlando
*Assistant Examiner* — Marta Dulko
(74) *Attorney, Agent, or Firm* — Nath, Goldberg & Meyer; Joshua B. Goldberg; Tanya E. Harkins

(57) ABSTRACT

A method and an apparatus for manufacturing an adhesive patch which is easily applied to the skin. The method includes a first step of forming a pressure-sensitive adhesive agent layer on a support, a second step of fixing a pinching piece forming sheet on a release sheet, a third step of forming a weakened part in the release sheet and the pinching piece forming sheet, and a fourth step of releasably adhering the release sheet to which the pinching piece forming sheet is fixed, that has been obtained in the third step, to the pressure-sensitive adhesive agent layer on the support, that has been obtained in the first step.

3 Claims, 15 Drawing Sheets

(51) Int. Cl.
  *B32B 37/12* (2006.01)
  *B32B 37/18* (2006.01)
  *A61F 13/02* (2006.01)
  *A61F 13/00* (2006.01)
  *A61K 9/70* (2006.01)

(52) U.S. Cl.
  CPC ......... *A61F13/0259* (2013.01); *A61F 13/0276* (2013.01); *A61F 2013/0296* (2013.01); *A61K 9/703* (2013.01); *Y10T 156/10* (2015.01); *Y10T 156/1052* (2015.01); *Y10T 156/12* (2015.01)

(56) References Cited

U.S. PATENT DOCUMENTS

| | | |
|---|---|---|
| 2,992,644 A | 7/1961 | Platinga et al. |
| 3,156,242 A | 11/1964 | Crowe, Jr. |
| 3,260,260 A | 7/1966 | Questel |
| 3,367,329 A | 2/1968 | Dibelius |
| 3,416,524 A | 12/1968 | Meier |
| 3,645,835 A | 2/1972 | Hodgson |
| 3,811,438 A | 5/1974 | Economou |
| 3,885,559 A | 5/1975 | Economou |
| 3,989,040 A | 11/1976 | Lofgren et al. |
| 4,265,234 A | 5/1981 | Schaar |
| 4,374,520 A | 2/1983 | Grossmann et al. |
| 4,513,739 A | 4/1985 | Johns |
| 4,600,001 A | 7/1986 | Gilman |
| 4,614,183 A | 9/1986 | McCracken et al. |
| 4,649,909 A | 3/1987 | Thompson |
| 4,664,106 A | 5/1987 | Snedeker |
| 4,685,455 A | 8/1987 | Vrouenraets |
| 4,743,232 A | 5/1988 | Kruger |
| 4,744,355 A | 5/1988 | Faasse, Jr. |
| 4,780,168 A | 10/1988 | Beisang et al. |
| 4,781,293 A | 11/1988 | Johns |
| 4,832,008 A | 5/1989 | Gilman |
| 4,915,227 A | 4/1990 | Johns |
| 4,915,228 A | 4/1990 | Johns |
| 4,917,928 A | 4/1990 | Heinecke |
| 4,917,929 A | 4/1990 | Heinecke |
| 4,950,282 A | 8/1990 | Beisang et al. |
| RE33,353 E | 9/1990 | Heinecke |
| 5,009,224 A | 4/1991 | Cole |
| 5,042,466 A | 8/1991 | McKnight |
| 5,052,381 A | 10/1991 | Gilbert et al. |
| 5,074,293 A | 12/1991 | Lott et al. |
| 5,088,483 A | 2/1992 | Heinecke |
| 5,147,698 A | 9/1992 | Cole |
| 5,153,040 A | 10/1992 | Faasse, Jr. |
| 5,360,393 A | 11/1994 | Garth et al. |
| 5,520,629 A | 5/1996 | Heinecke et al. |
| 5,527,271 A | 6/1996 | Shah et al. |
| D377,529 S | 1/1997 | Nyqvist-Mayer |
| 5,599,289 A | 2/1997 | Castellana |
| 5,637,080 A | 6/1997 | Geng |
| 5,653,699 A | 8/1997 | Reed et al. |
| D385,038 S | 10/1997 | Shultz |
| 5,683,354 A | 11/1997 | Levy |
| 5,713,842 A | 2/1998 | Kay |
| 5,733,251 A | 3/1998 | Johns |
| 5,820,578 A | 10/1998 | Johansen |
| 5,823,977 A | 10/1998 | Dalyea |
| 5,840,052 A | 11/1998 | Johns |
| D408,541 S | 4/1999 | Dunshee et al. |
| D409,754 S | 5/1999 | Dunshee et al. |
| D410,087 S | 5/1999 | Dunshee et al. |
| 5,979,450 A | 11/1999 | Baker et al. |
| 5,985,395 A | 11/1999 | Comstock et al. |
| 6,043,408 A | 3/2000 | Geng |
| 6,093,465 A | 7/2000 | Gilchrist et al. |
| D430,674 S | 9/2000 | Dunshee et al. |
| 6,120,792 A | 9/2000 | Juni |
| D433,140 S | 10/2000 | Nielsen |
| 6,149,614 A | 11/2000 | Dunshee et al. |
| 6,159,497 A | 12/2000 | LaPrade et al. |
| D454,955 S | 3/2002 | Dunshee et al. |
| D458,687 S | 6/2002 | Dale et al. |
| D473,947 S | 4/2003 | Jacobson |
| D474,842 S | 5/2003 | Wolsing et al. |
| 6,607,799 B1 | 8/2003 | Heinecke et al. |
| D480,144 S | 9/2003 | Adams et al. |
| D484,601 S | 12/2003 | Griffiths et al. |
| D484,602 S | 12/2003 | Griffiths et al. |
| 6,706,940 B2 | 3/2004 | Worthley |
| 6,742,522 B1 | 6/2004 | Baker et al. |
| D493,230 S | 7/2004 | Liedtke et al. |
| D495,419 S | 8/2004 | Dunshee |
| 6,797,855 B2 | 9/2004 | Worthley |
| D501,559 S | 2/2005 | Shaw et al. |
| D501,926 S | 2/2005 | Shaw et al. |
| D503,982 S | 4/2005 | Liedtke et al. |
| D511,005 S | 10/2005 | Liedtke et al. |
| D516,729 S | 3/2006 | Liedtke et al. |
| D557,424 S | 12/2007 | Knight |
| D572,824 S | 7/2008 | Propp |
| D573,260 S | 7/2008 | Dunshee |
| D578,651 S | 10/2008 | Dunshee |
| 7,442,849 B2 | 10/2008 | Heinecke |
| D604,423 S | 11/2009 | Dunshee |
| D604,424 S | 11/2009 | Coubetergues |
| D605,299 S | 12/2009 | Iwahashi et al. |
| D607,112 S | 12/2009 | Rogers et al. |
| D611,156 S | 3/2010 | Dunshee |
| D625,018 S | 10/2010 | Smith et al. |
| 7,812,212 B2 | 10/2010 | Propp et al. |
| 8,057,885 B2 | 11/2011 | Goyarts |
| 8,080,703 B2 | 12/2011 | Marcussen |
| 8,110,718 B2 | 2/2012 | Heinecke |
| 8,212,101 B2 | 7/2012 | Propp |
| D668,766 S | 10/2012 | Miyachi et al. |
| D670,395 S | 11/2012 | Wakamatsu et al. |
| D672,464 S | 12/2012 | Holm et al. |
| 8,691,355 B2 | 4/2014 | Funakoshi et al. |
| 2005/0034731 A1 | 2/2005 | Rousseau et al. |
| 2005/0039418 A1* | 2/2005 | Haws et al. ............... 53/412 |
| 2009/0124953 A1 | 5/2009 | Nakahara et al. |
| 2011/0229676 A1 | 9/2011 | Funakoshi et al. |
| 2011/0257574 A1 | 10/2011 | Svensby |

FOREIGN PATENT DOCUMENTS

| | | |
|---|---|---|
| CN | D300737239 S | 1/2008 |
| JP | 50-133797 | 4/1974 |
| JP | 59-149141 A | 8/1984 |
| JP | 8-112305 A | 5/1996 |
| JP | 9-238975 A | 9/1997 |
| JP | 2000-219622 A | 8/2000 |
| JP | 2002-531121 | 9/2002 |
| JP | 2002-531221 A | 9/2002 |
| JP | D1232725 S | 3/2005 |
| JP | 3754744 S | 3/2006 |
| JP | D1296123 S | 3/2007 |
| JP | 3135535 | 9/2007 |
| JP | 2008-264170 | * 11/2008 .............. A61F 13/02 |
| JP | 2008-264170 A | 11/2008 |
| JP | 2009-131583 A | 6/2009 |
| JP | D1378701 S | 12/2010 |
| JP | D1378702 S | 12/2010 |
| JP | D1380357 S | 12/2010 |
| JP | D1408441 S | 2/2011 |
| KR | D3001360890000 S | 1/1993 |
| KR | 100661889 B1 | 12/2006 |
| KR | D300476900.0001 S | 1/2008 |
| KR | D300496466.0000 S | 6/2008 |
| KR | 20080081065 A | 9/2008 |
| NL | 1001019 | 2/1997 |
| NL | 1001019 C2 | 2/1997 |
| RU | 2264207 C2 | 3/2004 |
| TW | D124495 S | 8/2008 |
| TW | D142505 S | 9/2011 |
| VN | D3-2007-00220 S | 6/2007 |
| VN | D3-2010-00235 S | 5/2010 |
| WO | 00/33776 A1 | 6/2000 |

(56) References Cited

FOREIGN PATENT DOCUMENTS

| WO | WO 00/33776 | * | 6/2000 | ............ A61F 13/02 |
| WO | WO 0033776 A1 | * | 6/2000 | ............ A61F 13/02 |
| WO | 2010/044152 A1 | | 4/2010 | |

OTHER PUBLICATIONS

International Preliminary Report on Patentability for PCT Application No. JP2010/067129; 6 pages; mailed May 24, 2012.
Office Action issued for Chinese Patent Application No. 201080045908.4 on Jun. 6, 2013.
Notice of Allowance issued for Taiwan Design Patent Application No. 099306087 on Jun. 21, 2011.
Notice of Allowance issued for Taiwan Design Patent Application No. 100302179 on Nov. 18, 2011.
Notice of Allowance issued for Design U.S. Appl. No. 29/356,253 on Jan. 18, 2013.
Office Action issued for Design U.S. Appl. No. 29/356,253 on Mar. 30, 2012.
Office Action issued for Design U.S. Appl. No. 29/390,774 on Jan. 17, 2013.
Office Action issued for Vietnamese Design Patent Application No. 3-2010-01527 on Apr. 6, 2012.
Notice of Allowance and Fees Due for U.S. Appl. No. 29/356,253, mailed by the U.S. Patent and Trademark Office on May 10, 2013.
Notice of Allowance and Fees Due for U.S. Appl. No. 29/379,795, mailed by the U.S. Patent and Trademark Office on May 13, 2013.
European Search Report for European Patent Application No. 10823292.7 dated Jul. 23, 2013, 5 pages.
U.S. Appl. No. 13/501,695, Official Action dated Aug. 7, 2014, fifty-six (56) pages.
Office Action in EP Patent Application No. 10823292.7 dated Mar. 24, 2014, Five(5) pages.
U.S. Appl. No. 13/501,695, Office Action dated Jan. 29, 2015, fourteen (14) pages.
Korean Patent Application No. 10-2012-7009846, Notice of Allowance dated Feb. 11, 2015, two (2) pages.
Russian Patent Application No. 2012119543, Notice of Allowance dated Sep. 2, 2014, six (6) pages.

* cited by examiner

METHOD AND APPARATUS FOR MANUFACTURING ADHESIVE PATCH

This is a National Phase Application filed under 35 U.S.C. 371 as a national stage of PCT/JP2010/067129, filed Sep. 30, 2010, an application claiming the benefit from the Japanese patent Application No. 2009-237571, filed Oct. 14, 2009, and No. 2009-261314, filed Nov. 16, 2009, and No. 2010-134407, filed Jun. 11, 2010, the content of each of which is hereby incorporated by reference in its entirety.

TECHNICAL FIELD

The present invention relates to an adhesive patch such as a poultice or a plaster, and in particular, to a method and an apparatus for manufacturing the adhesive patch.

BACKGROUND ART

An adhesive patch usually includes a support made of a woven fabric, a nonwoven fabric, or the like, a pressure-sensitive adhesive agent layer provided on one surface of the support, and a release sheet which is releasably attached to the pressure-sensitive adhesive agent layer. Further, a percutaneously absorbable drug and the like are contained in the pressure-sensitive adhesive agent forming the pressure-sensitive adhesive agent layer.

With respect to such an adhesive patch, ease in applying to the skin has been always required. Therefore, conventionally, adhesive patches as described, for example, in the following Patent Literatures 1 to 4 have been proposed.

The adhesive patches described in Patent Literatures 1 and 2 include a support having stretching properties and a release sheet releasably attached to a pressure-sensitive adhesive agent layer on the support, and a perforated line is formed in the central portion of the release sheet. At the time of using this adhesive patch, first, the adhesive patch is pulled to the right and left to rip the perforated line apart, to expose the pressure-sensitive adhesive agent layer. Then, the exposed portion is applied to the skin, and thereafter, the release sheet is removed.

Further, the adhesive patch described in Patent Literature 3 is an adhesive patch in which two release sheets are placed on a pressure-sensitive adhesive agent layer, and an inner end of one of the release sheets is folded, and an inner end of the other release sheet is superposed on the folded portion. In such an adhesive patch, because it is possible to pinch the folded portion or the end superposed thereon, it is possible to easily remove the release sheets from the pressure-sensitive adhesive agent layer, thereby easily applying to the skin.

Moreover, the adhesive patch described in Patent Literature 4 is an adhesive patch in which two release sheets are placed on a pressure-sensitive adhesive agent layer in a state in which the two release sheets are respectively folded so as to butt against each other with their folded lines. In this adhesive patch as well, in the same way as the adhesive patch described in Patent Literature 3, it is possible to pinch the folded portion to easily release the release sheets from the pressure-sensitive adhesive agent layer.

Further, the adhesive patch described in Patent Literature 5 is a wound dressing, that is a so-called adhesive plaster, which is different from an adhesive patch, and this is an adhesive patch which is designed for easily releasing of the release sheet. That is, this wound dressing is formed, in the same way as the adhesive patch described in Patent Literature 4, such that two release sheets are placed on a pressure-sensitive adhesive agent layer in a state in which the ends of the two release sheets butt against each other. Then, pull-tabs for pulling the release sheets to release the release sheets are adhered to the ends on the butting sides of the respective release sheets. In this wound dressing configured in this way as well, in the same way as the ones described in Patent Literatures 3 and 4, it is possible to pinch the pull-tabs to easily release the release sheets from the pressure-sensitive adhesive agent layer.

The above-described conventional adhesive patches and wound dressing are respectively improved in ease of application. However, in the adhesive patches described in Patent Literatures 1 and 2, when the exposed portion of the pressure-sensitive adhesive agent layer is applied to the skin after dividing the release sheet along the perforated line, it may be difficult to release the release sheet in some cases.

On the other hand, with respect to the adhesive patches described in Patent Literatures 3 and 4 and the wound dressing described in Patent Literature 5, there is the advantage that it is easy to release the release sheets from the pressure-sensitive adhesive agent layer because there are portions to be pinched. However, there is a problem that medicinal properties in the pressure-sensitive adhesive agent layer leak out of the superposed portion or the butting portion of the two release sheets.

Further, with respect to the adhesive patch described in Patent Literature 3, because the folded portion in the one of the release sheets and the end of the other release sheet superposed thereon are directed in the same direction, it is configured to be able to pinch the release sheet only from one side, which is inconvenient. Moreover, a special sheet folding device is required in order to fold the release sheets, which also brings about the problem of an increase in the cost of manufacturing the adhesive patch.

Also, with respect to the adhesive patch described in Patent Literature 4, a process of folding the release sheets during the manufacture thereof is necessary, and moreover, it is necessary to accurately butt the folding lines of the two release sheets in order to suppress leakage of the medicinal properties as low as possible, which makes it extremely difficult to manufacture the adhesive patch.

Further, with respect to the configuration described in Patent Literature 5, in the same way as the adhesive patch described in Patent Literature 4, it is necessary to accurately butt the release sheets and the pull-tabs. Further, even when the sheet material and the tab material are cut after the pull-tabs (tab material) before cutting are adhered to the release sheets (sheet material) before cutting, there is a problem that the portion with high strength at which both are adhered to one another is to be cut, and therefore, it is difficult to cut it.

Further, with respect to the wound dressing described in Patent Literature 5, because release sheets are separated with little resistance at the time of pulling the pull-tabs to release the release sheets, anti-releasing means for preventing releasing of the release sheets are provided at the edges of the wound dressing. Meanwhile, the manufacturing process increases one process or more by providing the anti-releasing means, which brings about the problem of requiring time and cost for manufacture. Further, as the anti-releasing means, there is a folding type (refer to FIG. 5 in Patent Literature 5) or a clip type (refer to FIG. 6 in Patent Literature 5). However, with these types, projecting portions are formed on the surface of the wound dressing, which may hinder applying it to an affected area. Therefore, such projecting portions are unsuitable for a large-size wound dressing such as a poultice or a plaster.

Furthermore, with respect to the configurations described in Patent Literatures 3 to 5, because the two release sheets are not combined, both may have a position gap, or may be turned up, and the medicinal properties easily leak out in such a case, which leads to the problem in view of stability in drug formulation. Further, a position gap between the release sheets deforms the support at the time of pulling the folded portions or the pull-tabs, which may bring about a problem of wrinkling at the time of application. Such a harmful effect due to a position gap becomes apparent in particular in the configurations described in Patent Literatures 4 and 5 in which the ends are merely brought to butt against each other.

As described above, there are various problems in the conventional technologies. Therefore, an adhesive patch which is easily applied to the skin and its manufacture is easy has been demanded.

CITATION LIST

Patent Literature

Patent Literature 1: Japanese Patent Application Laid-Open No. Hei-8-112305
Patent Literature 2: Japanese Published Unexamined Utility Model Application No. Sho-50-133797
Patent Literature 3: Japanese Patent Application Laid-Open No. 2000-219622
Patent Literature 4: Japanese Patent Application Laid-Open No. 2009-131583
Patent Literature 5: Japanese Patent Application Laid-Open No. Sho-59-149141

SUMMARY OF INVENTION

Technical Problem

In consideration of the above-described circumstances, the inventor, et. al., have devised a novel adhesive patch. An object of the present invention is to provide a method and an apparatus suitable for manufacturing the novel adhesive patch.

Solution to Problem

An adhesive patch manufactured by an adhesive patch manufacturing method or an adhesive patch manufacturing apparatus according to the present invention includes a support, a pressure-sensitive adhesive agent layer provided on one surface of the support, a release sheet which is releasably attached to the pressure-sensitive adhesive agent layer, and a weakened part which is formed in the release sheet, the weakened part being for easily dividing the release sheet into two parts, and further in the adhesive patch, a pinching piece forming sheet is fixed on the release sheet such that the pinching piece forming sheet covers the weakened part, and portions of the pinching piece forming sheet which are other than the at least one fixed portion function as pinching pieces, and in the pinching piece forming sheet, a weakened part for easily dividing the release sheet into two parts is formed at a position corresponding to the weakened part of the release sheet. In particular, the support preferably has stretching properties. This is because it is possible to divide the release sheet and the pinching piece forming sheet along the weakened parts by pulling the support.

In such an adhesive patch, pinching pieces are respectively formed in the divided respective release sheets by dividing the release sheet and the pinching piece forming sheet along the weakened parts. Therefore, it is possible for a user to easily release the release sheet from the pressure-sensitive adhesive agent layer by use of the pinching pieces, and further, the pieces may be utilized such as for positioning the adhesive patch. Further, the release sheet is configured as one sheet before use, and therefore, the problems of leakage of medicinal properties and wrinkling of the adhesive patch due to a position gap in the release sheet as release sheets in the conventional configurations described in Patent Literatures 3 to 5 do not occur.

Such an adhesive patch is manufactured by the following method. That is, a method for manufacturing the adhesive patch according to the present invention includes a first step of forming a pressure-sensitive adhesive agent layer on a support, a second step of fixing a pinching piece forming sheet on a release sheet, a third step of forming a weakened part in the release sheet and the pinching piece forming sheet, and a fourth step of releasably adhering the release sheet on which the pinching piece forming sheet is fixed, that has been obtained in the third step, to the pressure-sensitive adhesive agent layer on the support, that has been obtained in the first step. The fixing in the second step is preferably carried out by a heat-sealing method.

Further, the present invention relates to a method for continuously manufacturing adhesive patches, and in that case, the adhesive patches are manufactured from continuous webs respectively composing the support, the release sheet, and the pinching piece forming sheet. That is, the method includes a first step of unwinding a first continuous web which will be the support from a first original roll, to form a pressure-sensitive adhesive agent layer on the first continuous web, a second step of unwinding a second continuous web which will be the release sheet from a second original roll, unwinding a third continuous web which will be the pinching piece forming sheet from a third original roll, and superposing the third continuous web on the second continuous web to fix both sheets, a third step of forming a weakened part in the second continuous web and the third continuous web which are fixed, a fourth step of releasably adhering the second continuous web to which the third continuous web is fixed, that has been obtained in the third step, to the pressure-sensitive adhesive agent layer on the first continuous web, that has been obtained in the first step, so as to form a laminated body, and a fifth step of cutting out the laminated body obtained in the fourth step to a predetermined size, so as to form the adhesive patch. In this case as well, the fixing in the second step is preferably carried out by a heat-sealing method.

In addition, as a place in which the weakened parts is formed, in the case where there is one fixed portion, the weakened parts may be on the fixed portion. However, in the case where fixed portions are provided at two places, the weakened parts are preferably formed between the two fixed portions. This is because the stiffness or the strength of the fixed portion is higher than that of the place other than the fixed portion, which makes it possible to easily form the weakened parts between the two fixed portions.

Further, in the case where the release sheet (the second continuous web) and the pinching piece forming sheet (the third continuous web) are fixed by heat-sealing, the release sheet and/or the pinching piece forming sheet is possibly shrunk. However, in the case where the fixed portion is narrower, it is possible to suppress such shrinkage. Based on this point, it is extremely effective to form fixed portions at two places, which decreases the widths of the fixed portions.

Further, another aspect of the present invention relates to an adhesive patch manufacturing apparatus, the adhesive patch manufacturing apparatus includes a spreading and adhering unit which spreads and adheres a pressure-sensitive adhesive agent on a first continuous web which is unwound from a first original roll, to be the support, to form a pressure-sensitive adhesive agent layer, a fixing unit which superposes a second continuous web which is unwound from a second original roll, to be the release sheet, and a third continuous web which is unwound from a third original roll, to be the pinching piece forming sheet, to fix both sheets, a weakened part forming unit which forms a weakened part in the second continuous web and the third continuous web fixed by the fixing unit, a laminated body forming unit which releasably adheres the second continuous web to which the third continuous web is fixed, which has passed through the weakened part forming unit, to the pressure-sensitive adhesive agent layer on the first continuous web, which has passed through the spreading and adhering unit, so as to form a laminated body, and a cutting unit which cuts out the laminated body obtained by the laminated body forming unit, to a predetermined size, so as to form the adhesive patch.

The fixing unit preferably includes a heat-sealing device. Further, in the case where the heat-sealing device is a press type, a first accumulation device and a second accumulation device which are capable of accumulating the second continuous web and the third continuous web are preferably respectively provided on the upstream side of the heat-sealing device, and between the heat-sealing device and the laminated body forming unit. By providing such accumulation devices, during fixing of the second continuous web and the third continuous web by the heat-sealing device, it is possible to temporarily accumulate the second continuous web and the third continuous web which are continuously fed from the second original roll and the third original roll by the first accumulation device, and therefore, there is no need to stop feeding the second continuous web and the third continuous web. Further, it is possible to continuously feed the second continuous web and the third continuous web which are accumulated by the second accumulation device to the downstream side, and it is possible to perform the continuous manufacturing processes uninterruptedly, which makes it possible to improve the efficiency of the manufacture of adhesive patches.

Advantageous Effects of Invention

In the adhesive patch according to the present invention, there is no member for which folding processing is necessary. Therefore, in the manufacturing method and apparatus as well, a special folding device or the like is not necessary, and its manufacture is easy. Further, because anti-releasing means as described in Patent Literature 5 as well is not necessary, its manufacture is easy in view of this point. Therefore, the efficiency of manufacture is improved, which makes it possible to suppress an increase in the cost of manufacturing.

DESCRIPTION OF EMBODIMENTS

Hereinafter, preferred embodiments of the present invention will be described in detail with reference to the drawings.

[Adhesive Patch Manufactured by Manufacturing Method and Manufacturing Apparatus According to the Present Invention]

Figure 1:
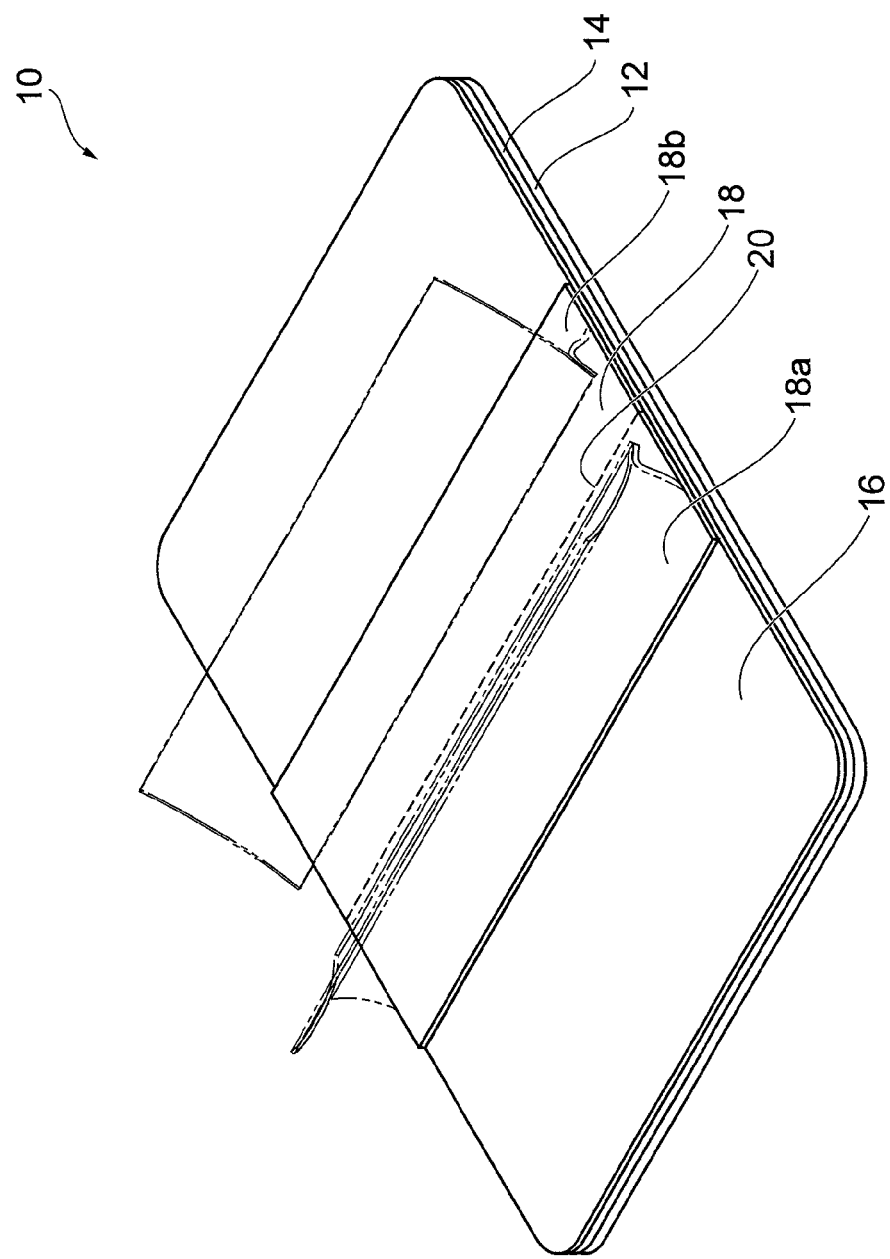
FIG. 1 is a perspective view schematically showing an embodiment of an adhesive patch manufactured by a method and an apparatus for manufacturing according to the present invention.
Figure 2:
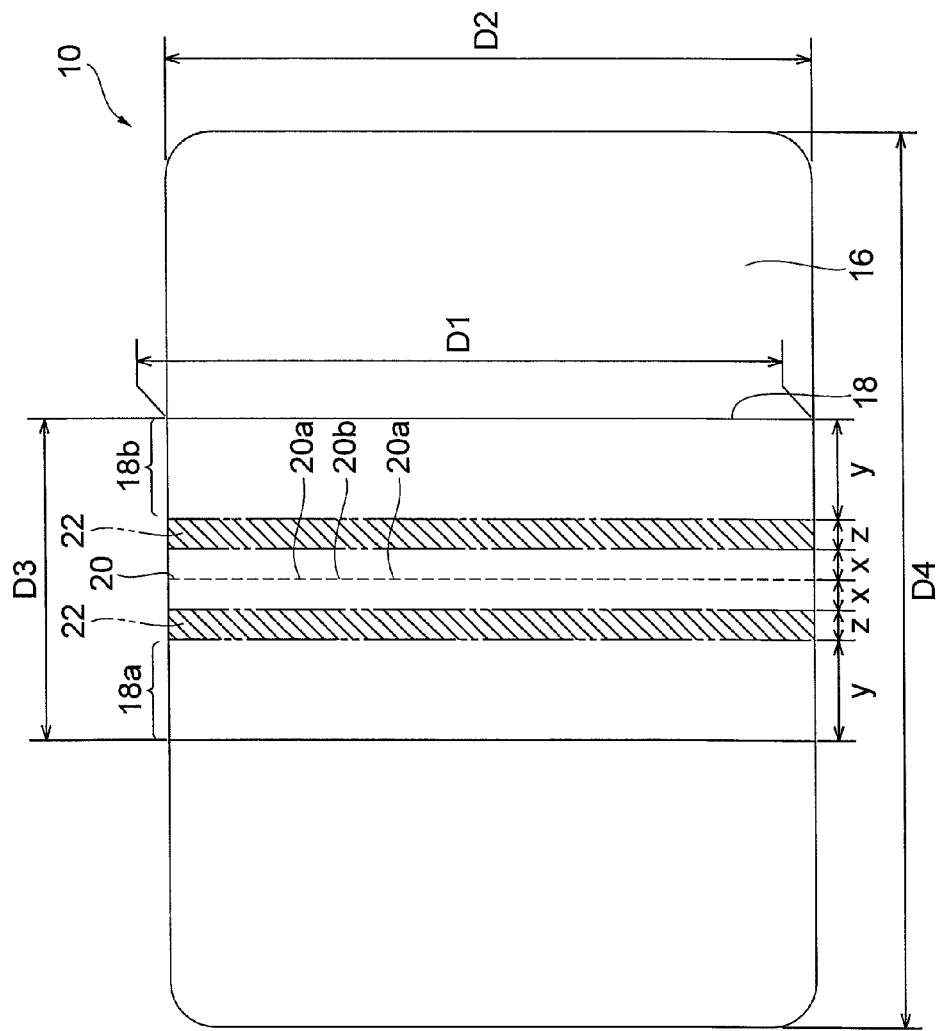
FIG. 2 is a plan view showing the adhesive patch of FIG. 1.
Figure 3:
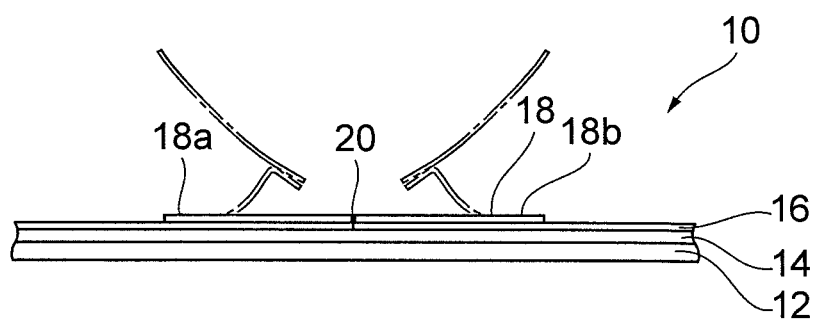
FIG. 3 is a side view showing the adhesive patch of FIG. 1.

First, an adhesive patch manufactured by an adhesive patch manufacturing method and an adhesive patch manufacturing apparatus according to the present invention will be described. FIG. 1 is a perspective view showing an embodiment of the adhesive patch, FIG. 2 is a plan view thereof, and FIG. 3 is a side view thereof. An illustrated adhesive patch 10 is used as a poultice or a plaster, or the like, and is composed of a support 12 having stretching properties, a pressure-sensitive adhesive agent layer 14 containing a drug, which is formed on substantially the entire surface of one surface of the support 12, a release sheet 16 which is releasably attached to the surface of the pressure-sensitive adhesive agent layer 14, and a pinching piece forming sheet 18 fixed to the release sheet 16.

The pinching piece forming sheet 18 is not fixed to the release sheet 16 with its entire surface, and both right and left edge portions are in a state of being non-fixed to the release sheet 16.

Moreover, weakened parts 20 such as perforated lines for easily dividing the release sheet 16 and the pinching piece forming sheet 18 are formed from one long side to the other long side of the adhesive patch 10 in substantially the central portion of the release sheet 16 and the pinching piece forming sheet 18 (which is substantially the central portion in the longitudinal direction of the adhesive patch 10, hereinafter a case of referring "substantially the central portion" is the same).

Hereinafter, respective components will be described.

With respect to the support 12, an appropriate sheet-like member such as a woven fabric, a knit fabric, a nonwoven fabric, a nonwoven paper, or a film may be used as long as it has stretching properties, and the support 12 is selected in consideration of the physical properties such as its thickness, stretch, tensile strength, and workability for application, and the feeling of application, the occluding characteristic for skin, the transition of medicinal properties to the support 12, and the like. In addition, the stretching properties of the support 12 are preferably 50% in a lengthwise or machine feeding direction and/or a crosswise or transverse direction, and its modulus is preferably 0.5 to 10N/50 mm.

As a specific material of the support 12, bast fiber such as paper, cotton, hemp, or jute, cellulose fiber such as veins of a leaf fiber of Manila hemp or the like, animal fiber such as sheep wool, natural fiber such as protein fiber of silk fiber or feather fiber, regenerated cellulose fiber such as rayon or cuprammonium, regenerated fiber such as regenerated protein fiber, semisynthetic fiber such as cellulose acetate fiber or promix, nylon/aramid fiber, polyethylene terephthalate fiber, polyester fiber, acrylic fiber, polyolefine fiber such as polyethylene or polypropylene, polyvinyl alcohol fiber, polyvinyl chloride fiber, polyvinylidene chloride fiber, polyvinyl chloride-based fiber, polyurethane fiber, polyoxymethylene fiber, polytetrafluoroethylene fiber, poly-para-phenylenebenzbisthiazole (PBT) fiber, polyimide fiber, or the like may be utilized. In particular, a nonwoven fabric formed of polyester-based polyethylene terephthalate fiber which has little interaction with the ingredient contained in the pressure-sensitive adhesive agent layer 14 is preferable.

The pressure-sensitive adhesive agent layer 14 is for effectively utilizing the adhesive patch 10 such as a poultice or a plaster by containing or attaching, etc., a drug in or to an adhesive base. Further, as an adhesive ingredient which is a constitutional material of the pressure-sensitive adhesive agent layer 14, this is not limited in particular as long as it has adherence property to be able to be applied to the skin. In the case where the adhesive patch 10 is used as a poultice, the pressure-sensitive adhesive agent layer 14 preferably satisfies the conditions that the pressure-sensitive adhesive agent layer 14 has high skin adhesion, enhances the absorption of active ingredients through skin, contains as much moisture as practicable as possible, draws heat from the skin when the moisture in the pressure-sensitive adhesive agent layer 14 vaporizes, but gives a sensation of coolness due to this amount of heat generation, and the horny layer is hydrated by water molecules vaporizing from the inside, to accelerate the absorption of the drug, and the pressure-sensitive adhesive agent layer 14 does not go slack at normal temperature or around normal temperature, does not hurt and does not leave the skin sticky when releasing it, and is gumless, and the like. For this reason, a water-soluble polymer is preferably used for the pressure-sensitive adhesive agent layer 14, which contains a thickening agent of 5 to 20% by weight, and preferably of 10 to 15% by weight, a wetting agent of 5 to 40% by weight, a filler of 20% or less by weight, water of 10 to 80% by weight, a solubilizing agent of 0 to 8% by weight, a drug of 5% or less by weight, and preferably of 0.1 to 5% by weight.

As the aforementioned water-soluble polymer, gelatin, agar, alginic acid, mannan, carboxymethylcellulose or salt thereof, hydroxypropylcellulose or salt thereof, polyvinyl alcohol, polyacrylic acid or salt thereof, or one in which at least one of those is cross-linked by an organic or an inorganic cross-linking agent is preferably used.

In addition to the above-described adhesive base, a thickening agent, a wetting agent, and the like may be appropriately added to the pressure-sensitive adhesive agent layer 14.

For example, as a thickening agent, it is desirable to stably retain moisture of 10% to 80%, and desirable to have water retention capability. As a specific example of the thickening agent, water-soluble polymers of natural polymers such as plant polymers of guar gum, locust bean gum, carrageenan, alginic acid, alginic acid sodium salt, agar, gum arabic, tragacanth gum, karaya gum, pectin, starch, gum acacia, and the like, microbial polymers of xanthan gum and the like, and animal polymers of gelatin, collagen, and the like, semisynthetic polymers such as cellulose polymers of methylcellulose, ethylcellulose, hydroxyethyl cellulose, carboxymethylcellulose sodium, and the like, starch-derived polymers of amylogen, carboxymethyl starch, dialdehyde starch, and the like, synthetic polymers such as vinyl polymers of polyvinyl alcohol, polyvinylpyrrolidone, poly(vinyl methacrylate), and the like, acrylic-type polymers of polyacrylic acid or sodium polyacrylate, and the like, and further, of polyethylene oxide, or a methyl vinyl ether/maleic anhydride copolymer, and the like, may be preferably used. In particular, sodium polyacrylate is preferable. This is because it has high gel strength, and is excellent in water retention capability. Moreover, sodium polyacrylate with an average degree of polymerization of 20000 to 70000 is preferable. As the average degree of polymerization decreases to be lower than 20000, there is a tendency that the thickening effect weakens, which makes it impossible to obtain a sufficient gel strength, and as the average degree of polymerization increases to be higher than 70000, there is a tendency that the thickening effect strengthens, which reduces the workability. Further, by using in combination two types or more of the water-soluble polymers, for example, a polymer complex is formed with the strong ion polymer of sodium polyacrylate, thereby it is possible to obtain an elastic gel with stronger gel strength.

As a wetting agent, polyhydric alcohol or the like such as glycerin, propylene glycol, or sorbitol may be added, and as a filler, kaolin, talc, titanium, bentonite, aluminum silicate, titanium oxide, zinc oxide, aluminum metasilicate, calcium sulfate, calcium phosphate, or the like may be added. Further, as a solubilizing agent or an absorption promoter, propylene carbonate, crotamiton, 1-menthol, mint oil, limonene, diisopropyl adipate, or the like may be added. As a medicinal adjuvant agent, methyl salicylate, glycol salicylate, 1-menthol, thymol, mint oil, nonylic acid vanillylamide, Capsicum extract, or the like may be added.

Moreover, a stabilization agent, an antioxidant agent, an emulsifying agent, or the like may be added as needed. In addition, a cross-linking agent, polymerization agent, or the like may be added as needed. Those capable of consolidating the pressure-sensitive adhesive agent layer 14, and providing the water retention capability thereto may be added. These cross-linking agent and polymerization agent are appropriately selected according to a type of the thickening agent or the like. For example, in the case where polyacrylic acid or polyacrylate is applied to the thickening agent, a compound having at least two epoxy groups in its molecule, inorganic acid salt such as hydrochloride salt of Ca, Mg, Al or the like, sulfate salt, phosphoric salt or carbonate, organic acid salt such as citric salt, tartrate, gluconate or stearate, oxide such as zinc oxide or silicic anhydride, and a polyvalent metal compound of hydroxide such as aluminum hydroxide or magnesium hydroxide, and the like is preferably used. Further, in the case where polyvinyl alcohol is applied to the thickening agent, a complex compound such as adipic acid, thioglycollic acid, an epoxy compound (epichlorohydrin), aldehydes, an N-methylol compound, a complex compound of Al, Ti, Zr, Sn, V, Cu, B, Cr, and the like is preferably used. Further, in the case where polyvinyl pyrrolidone is applied to the thickening agent, a methyl vinyl ether/maleic anhydride copolymer, a polyacid compound, or alkali metal salt thereof (polyacrylic acid or tannic acid, and a derivative thereof), or the like is preferably used. Further, in the case where polyethylene oxide is applied to the thickening agent, peroxide, polysulfone azide, or the like is preferably used. Further, in the case where a methyl vinyl ether/maleic anhydride copolymer is applied to the thickening agent, a multifunctional hydroxy compound, polyamine, iodine, gelatin, polyvinyl pyrrolidone, iron, hydrargyrum, lead salt, or the like is preferably used. Further, in the case where gelatin is applied to the thickening agent, aldehydes such as formaldehyde, glutaraldehyde, and dialdehyde starch, diepoxides such as glyoxal or butadiene oxide, diketones such as divinyl ketone, diisocyanates, or the like is preferably used. Further, in the case where sodium polyacrylate is applied to the thickening agent, as a cross-linking agent, lithium hydroxide, multivalent metal salt such as zinc hydroxide, aluminum hydroxide or sodium borate and the like is preferably added. In particular, zinc salt and aluminum salt is preferable. A concentration of multivalent metal salt to be added as a cross-linking agent is preferably 0.5 to 1.5 equivalents with respect to one equivalent of a thickening agent (or water-soluble polymer). As the concentration of multivalent metal salt decreases to be lower than 0.5 equivalents, there is a tendency that the reaction is too slow, to reduce the gel strength, and as the concentration of multivalent metal salt increases to be higher than 1.5 equivalents, there is a tendency that the reaction is too fast, to be not uniform in gelatinization, and reduce the workability.

On the other hand, in a case of a plaster, as an adhesive base, rubber-based adhesive ingredients, acrylic-based adhesive ingredients, silicone-based adhesive ingredients, or the like are preferably used.

As rubber-based adhesive ingredients, both of natural rubber and synthetic rubber may be used, and as synthetic rubber, for example, a styrenic block copolymer or polyisobutylene may be cited. Moreover, as a styrenic block copolymer, a styrene-butylene-styrene block copolymer (SBS), a styrene-isoprene-styrene block copolymer (SIS), a styrene-ethylene/butylene-styrene block copolymer (SEBS), or a styrene-ethylene/propylene-styrene block copolymer (SEPS) may be cited. As a specific example of a styrenic block copolymer, a linear triblock copolymer such as KRATON D-1112, D-1111, and D-1107 (trade names, manufactured by Kraton Polymers Japan Ltd.), JSR5000 or JSR5002 (trade names, manufactured by JSR Corporation), Quintac 3530, 3421, or 3570C (trade names, manufactured by ZEON CORPORATION), KRATON D-KX401CS or D-1107CU (trade names, manufactured by Kraton Polymers Japan Ltd.), or a star-branched block copolymer, etc., such as KRATON D-1124 (trade name, manufactured by Kraton Polymers Japan Ltd.), or SOLPRENE 418 (trade name, manufactured by Phillips Petroleum Co.) may be cited.

As polyisobutylene, for example, macromolecular to low molecular polyisobutylene is used. For example, Oppanol B10, B12, B12SF, B15, B15SF, B30SF, B50, B50SF, B80, B100, B120, B150, or B200 (trade names, manufactured by BASF Japan Ltd.), Vistanex LM-MS, LM-MH, LM-H, MM L-80, MM L-100, MM L-120, or MM L-150 (trade names, manufactured by Exxon Mobil Corporation) or the like may be cited.

Further, as an acrylic-type polymer, a polymer or a copolymer, etc., which contains at least one (metha)acrylic acid ester which is represented by as a monomer unit, for example, 2-ethylhexyl acrylate, methyl acrylate, butyl acrylate, hydroxyethyl acrylate, 2-ethlhexyl methacrylate, or the like is used. For example, a pressure-sensitive adhesive agent of an acrylic acid/octyl acrylate copolymer, a 2-ethylhexyl acrylate/N-vinyl-2-pyrolidone/dimethacrylate-1,6-hexane glycol dimethacrylate copolymer, a 2-ethylhexyl acrylate/vinyl acetate copolymer, a 2-ethylhexyl acrylate/vinyl acetate/acrylic acid copolymer, a 2-ethylhexyl acrylate/2-ethlhexyl methacrylate/dodecy methacrylate copolymer, a methyl acrylate-2-ethylhexyl acrylate copolymer resin emulsion, an acrylic-type polymer contained in acrylic resin alkanolamine solution, or the Duro-Tak acrylic pressure-sensitive adhesive agent series (manufactured by National Starch and Chemical Company), the GELVA acrylic pressure-sensitive adhesive agent series (manufactured by Monsanto Company), the SK-Dyne Matriderm (manufactured by Soken Chemical & Engineering Co., Ltd.), the Eudragit series (manufactured by HIGUCHI INC.), or the like may be used.

The above-described rubber-based, acrylic-based, or silicone-based adhesive base may be singularly used or two of those may be mixed to be used.

Further, in a case of a plaster, tackifier resin, a plasticizing agent, a filler, and a stabilization agent may be appropriately compounded therein.

As a drug contained in the pressure-sensitive adhesive agent layer 14, this is not limited in particular as long as it is percutaneously absorbed into the body to exert its pharmacological effect. For example, an anti-inflammatory agent, an analgesic drug, an antihistamine, a local anesthetic, a blood circulation promoter, an anesthetic, an ataractic drug, an antihypertensive agent, an antibacterial agent, a vasodilator, or the like may be cited.

In detail, as a drug, at least one nonsteroidal anti-inflammatory agent, which is selected from methyl salicylate, glycol salicylate, 1-menthol, capsicum extract, nonylic acid vanillylamide, mint oil, diclofenac, ibuprofen, indometacin, ketoprofen, loxoprofen, sulindac, tolmetin, lobenzarit, penicillamine, fenbufen, flurbiprofen, naproxen, pranoprofen, tiaprofenic acid, suprofen, felbinac, ketorolac, oxaprozin, etodolac, zaltoprofen, piroxicam, pentazocine, buprenorphine hydrochloride, butorphanol tartrate, and the like, and an ester derivative or salt thereof, or a steroid anti-inflammatory agent such as prednisolone, dexamethasone, hydrocortisone, betamethasone, fluocinonide, fluocinolone acetonide, prednisolone valerate acetate, dexamethasone dipropionate, diflucortolone valerate, difluprednate, betamethasone valerate, hydrocortisone butyrate, clobetasone butyrate, betamethasone butyrate, propionic acid clobetasone, succinic acid dexamethasone, prednisolone 21-(2E,6E) farnesylate, hydrocortisone valerate, diflorasone diacetate, propionic acid dexamethasone, betamethasone dipropionate, amcinonide, dexamethasone valerate, halcinonide, budesonide, alclometasone dipropionate, or the like may be cited. However, this is not limited to those. Two or more drugs may be used together as needed. Further, these drugs may be contained in or attached to the pressure-sensitive adhesive agent layer 14 in the form of a compound which is induced into an ester body, a compound which is induced into an amide body, a compound which is induced into an acetal body, or inorganic salt or organic salt which is medically allowed as needed. An amount of the drug is appropriately selected according to a type and usage, and the like of the adhesive patch 10 such as a poultice or a plaster so as to apply an effective amount set in advance to the skin at the time of applying it to a patient.

As the release sheet 16, in addition to polypropylene, for example, casted polypropylene or oriented polypropylene, a colorless or colored sheet such as plastic film of polyethylene terephthalate, polybutylene terephthalate, polyethylene, polyester, polyurethane, polyvinyl chloride, polystyrene, or the like, silicone-treated paper that silicone processing is applied to synthetic resin, a synthetic paper, synthetic fiber, or the like, laminated-treated paper that an aluminum foil or a craft paper is laminated with polyethylene or the like, is used.

The thickness of the release sheet 16 is not limited in particular, and is preferably formed within a range of 10 µm to 75 µm, and preferably 12 µm to 50 µm. When the thickness of the release sheet 16 is thinner than 10 μm, the release sheet 16 is too thin, and therefore, the release sheet 16 tends to tangle on the pressure-sensitive adhesive agent layer 14 at the time of releasing it, or the release sheet 16 tends to be immediately divided at the time of manufacture, which reduces the workability and the like, or the release sheet 16 tends to easily wrinkle in the case where the release sheet 16 is adhered to the pressure-sensitive adhesive agent layer 14. Further, although it will be described in detail in the following, in use of the adhesive patch 10 according to the present invention, the release sheet 16 and the pinching piece forming sheet 18 are divided along the weakened parts 20 by pulling to the right and left. Meanwhile, when the thickness of the release sheet 16 is thicker than 75 μm, it is difficult to divide the release sheet 16 and the pinching piece forming sheet 18, and it is difficult to cut the original material web at the time of manufacture, which starts showing a tendency to reduce the workability and the like.

Moreover, although not shown in the drawings, it is preferable to add concavity and convexity to the release sheet 16 by embossing or the like. Further, in order to make the method of division clear, indicated parts of graphics such as arrows or letters, marks, etc., may be provided or coloring, etc., may be applied on the right and left portions of the release sheet 16. The indicated parts may be formed by embossing.

In the case where the release sheet 16 is embossed, the following function effects are exerted. That is, by forming concavity and convexity on the surface of the release sheet 16 by embossing, the concavity and convexity may increase the frictional resistance with fingers or the pressure-sensitive adhesive agent layer 14. Therefore, the effect that the concavity and convexity on the release sheet 16 serve as friction to easily get stuck by fingers at the time of dividing the release sheet 16 and the pinching piece forming sheet 18, is exerted. Further, because the frictional resistance between the release sheet 16 and the pressure-sensitive adhesive agent layer 14 increases, at the time of pulling the adhesive patch 10 to the right and left, the force reliably reaches the release sheet 16, which makes it easy to divide the release sheet 16. Moreover, because the thickness of the release sheet 16 varies depending on positions due to the concavity and convexity by embossing, the ends of the release sheet 16 along the dividing line tend to naturally detach from the pressure-sensitive adhesive agent layer 14 after dividing the release sheet 16, and this also makes it easy to release the release sheet 16.

In addition, due to such a detaching phenomenon of the ends of the release sheet 16, the exposed portions of the support 12 may be curved or the pressure-sensitive adhesive agent layer 14 corresponding to the portions may be adhered to one another. However, because the pinching piece forming sheet 18 (pinching pieces 18a and 18b) is fixed along the weakened part 20 of the release sheet 16, it is possible to prevent the ends of the release sheet 16 from detaching inadvertently from the pressure-sensitive adhesive agent layer 14.

The pinching piece forming sheet 18 is rectangular in shape in the illustrated embodiment, and a length of its long side D1 is substantially the same as the length of a short side D2 of the adhesive patch 10, and the length of a short side D3 is shorter than the length of a long side D4 of the adhesive patch 10. The pinching piece forming sheet 18 formed in this way is arranged such that the long sides of the pinching piece forming sheet 18 are parallel to the short sides of the release sheet 16 in substantially the central portion of the release sheet 16. The pinching piece forming sheet 18 is fixed to the release sheet 16 so as to be substantially unable to be separated at a position at predetermined spaces x (which are not limited in particular, but for example, 0.5 to 25 mm) on the right and left both sides from the longitudinally central axis (the position of the weakened part 20). Each of the right and left fixed portions 22 between the pinching piece forming sheet 18 and the release sheet 16 preferably extends over the entire length of the pinching piece forming sheet 18. Further, the pinching piece forming sheet 18 is not fixed to the release sheet 16 with respect to the portions on the outer side of the respective fixed portions 22 (in the directions departing away from the longitudinally central axis of the pinching piece forming sheet 18), and those non-fixed portions are to function as the pinching pieces 18a and 18b which will be described later. Because those pinching pieces 18a and 18b are to be pinched by fingers, they are appropriately determined as long as its size is able to be pinched by fingers. However, a width y of each of the pinching pieces 18a and 18b is preferably approximately 2 to 4 cm. This is because, when the width y is shorter than 2 cm, it is difficult to pinch the pinching pieces by fingers, and when the width y is longer than 4 cm, the pinching pieces 18a and 18b are too large to handle, and its material cost is increased.

A width z of the fixed portions 22 between the pinching piece forming sheet 18 and the release sheet 16 may be appropriately determined as long as a minimum size in which fixing of both sheets 16 and 18 is unable to be separated is ensured. Meanwhile, in order to effectively transfer the force from the pinching piece forming sheet 18 to the release sheet 16 at the time of dividing the sheet which will be described later, it is effective to have a constant width. For example, the width z is preferably approximately 0.1 to 10 mm.

In addition, in a case of the adhesive patch 10 with the length of the short side D2 of 150 mm, and the length of the long side D4 of 200 mm, a sheet with the length of the long side D1 of 150 mm, and the length of the short side D3 of 70 mm is preferably used as the pinching piece forming sheet 18, and a sheet in which the spaces x from the longitudinally central axis of the pinching piece forming sheet 18 (the position of the weakened part 20) to the fixed portions 22 are set to 2.5 mm, and the widths z of the fixed portions 22 are set to 1.0 mm, and therefore, widths y of the pinching pieces 18a and 18b are set to 31.5 mm is preferably used.

As means for fixing the pinching piece forming sheet 18 and the release sheet 16, any means may be used as long as it is possible to fix both sheets 16 and 18 so as to be substantially unable to be separated. Meanwhile, a method using an adhesive, a heat-sealing method or the like is preferable. In particular, in a case of a heat-sealing method, it is preferable for the reason that it is possible to significantly shorten a fixing time, etc., as compared with a case of using an adhesive.

Further, the fixed portions 22 are in the form of continuous lines in the drawing. However, the fixed portions 22 may be in the form of discontinuous lines such as dotted lines.

Figure 4:
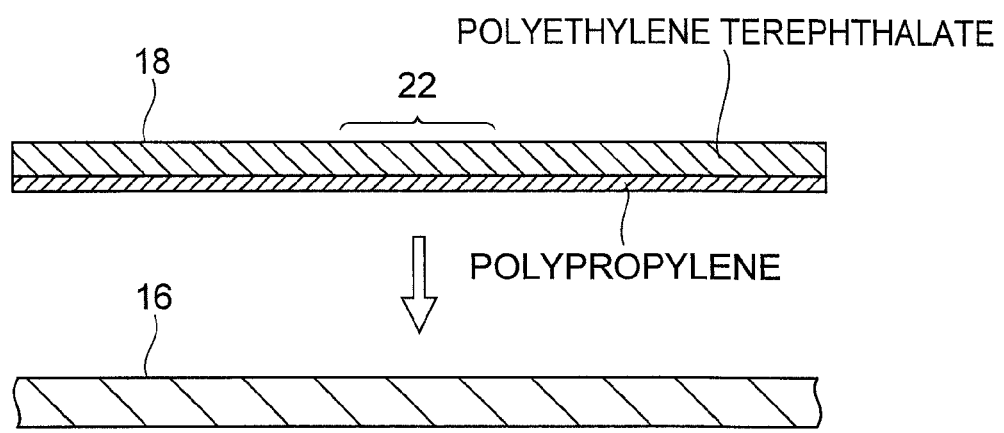
FIG. 4 is a cross-sectional view schematically showing a pinching piece forming sheet of a two-layered structure.

Moreover, as a material of the pinching piece forming sheet 18, a material which is the same as that of the release sheet 16 described above may be used. However, in particular, in consideration of the function as pinching pieces, polyethylene terephthalate, which is unable to be easily ripped, is effective. However, in the case where the release sheet 16 has a single layer structure of polyethylene terephthalate, and at least the surface layer of the release sheet 16 is made of polypropylene and concavity and convexity is formed thereon by embossing or the like, it may be difficult to heat-seal both in some cases. In that case, an adhesive may be used. However, in order to carry out heat-sealing, the pinching piece forming sheet 18 may be formed into a two-layered structure as schematically shown in FIG. 4. That is, by laminating polypropylene on the bottom surface of the base layer of polyethylene terephthalate (the surface on the side of the release sheet 16), it is possible to easily carry out heat-sealing with respect to the release sheet 16 of polypropylene having concavity and convexity as well.

In addition, the thickness of the pinching piece forming sheet 18 may be appropriately determined. However, in consideration of the strength as pinching pieces, the feeling at the time of pinching it, and the like, the thickness is preferably approximately 10 to 100 μm. Further, in the case of a two-layered structure of polyethylene terephthalate and casted polypropylene, the polyethylene terephthalate layer is 5 to 40 μm, and the casted polypropylene layer is approximately 10 to 60 μm. In the case where an oriented polypropylene layer is used in place of the casted polypropylene layer, the thickness of the oriented polypropylene layer is preferably approximately 10 to 60 μm.

Further, by coloring the pinching piece forming sheet 18 or the portions to be the pinching pieces 18a and 18b with a color different from that of the release sheet 16, it is possible to easily distinguish the pinching pieces 18a and 18b from the release sheet.

The weakened parts 20 formed in substantially the central portion of the release sheet 16 and the pinching piece forming sheet 18 are for easily dividing both sheets 16 and 18, and is formed over the entire length of the pinching piece forming sheet 18. In the present embodiment, as clearly shown in FIG. 2, the weakened part 20 is a so-called perforated line in which perforations 20a penetrating through the release sheet 16 and the pinching piece forming sheet 18 are continuously formed. The configuration of the perforated line may be appropriately determined. However, a ratio of lengths between the perforation 20a and a connecting region 20b between the perforations 20a is preferably "20a":"20b"=1 to 1500:1 to 25, and is more preferably "20a":"20b"=1 to 1000:1 to 20, and is furthermore preferably "20a":"20b"=100 to 1000:1 to 10. When the length of the perforation 20a is longer than the length of the connecting region 20b out of the above-described range, the sheets may be divided even when not in use, and the medicinal properties vaporize to reduce its medicinal effect, and the like, that starts showing a tendency to decrease the convenience and workability and the like. In addition, it is possible to prevent or suppress evaporation of the medicinal properties and moisture from the perforations 20a by tensioning the release sheet 16 to close the perforations 20a. On the other hand, when the length of the perforation 20a is shorter than the length of the connecting region 20b out of the above-described range, there is a tendency that it is difficult to divide the release sheet 16, to decrease the reliability and convenience. Further, the length of the connecting region 20b as well may be appropriately determined. However, the length of the connecting region 20b is preferably within a range of 0.03 to 10 mm. When the connecting region 20b gets too long, it is difficult to divide the sheet. On the other hand, when the connecting region 20b is short, it is easy to divide the sheet. However, when the connecting region 20b is too short, the sheet is easily torn even when not in use.

Figure 5:
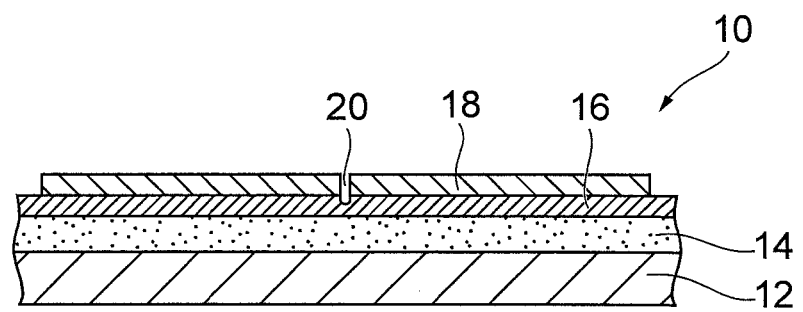
FIG. 5 is a partial cross-sectional view of the adhesive patch showing a modified example of a weakened part.

In addition, because the weakened parts 20 are for easily dividing the release sheet 16 and the pinching piece forming sheet 18, a groove as shown in FIG. 5 may be formed in place of the perforated line. This groove penetrates through the pinching piece forming sheet 18 to extend part of the way of the release sheet 16 that is a so-called half-cut. Therefore, the weakened part 20 made by a groove in this way has the advantage that there is no problem of leakage of medicinal properties as that in the perforated line. In addition, as the weakened parts 20, as one in which the release sheet 16 and the pinching piece forming sheet 18 are locally heated by a laser or the like, to make the portion be easily divided, thinning of the films, and the like may be variously conceived of.

In consideration of division of the release sheet 16 and the pinching piece forming sheet 18 along the weakened parts 20, the tensile strength of the release sheet 16 is not limited in particular. However, it is within a range of 1 g/cm to 200 g/cm, and preferably within a range of 1 g/cm to 100 g/cm. This range is based on the fact that the material of the pinching piece forming sheet 18 fixed to the release sheet 16 is preferably polyethylene terephthalate or the like, which has stiffness higher than that of the release sheet 16. That is, even when the tensile strength of the release sheet 16 having the weakened part 20 is low at approximately 1 g/cm, because the pinching piece forming sheet 18 is fixed to the release sheet 16, moderate dividing property is provided. On the other hand, as the tensile strength of the release sheet 16 is decreased to be less than 1 g/cm, the release sheet 16 is cut off in the process at the time of manufacture, and it is impossible to continuously adhere the release sheet 16 to the pressure-sensitive adhesive agent layer 14. Further, in the case where the adhesive patch 10 such as a poultice or a plaster is put in a packing bag, the release sheet 16 easily shows a tendency to be easily divided, which decreases a yield ratio. In contrast, as the tensile strength is increased to be greater than 200 g/cm, the release sheet 16 shows a tendency to be difficult to divide in use, which reduces the convenience.

Next, the usage of the adhesive patch 10 as described above will be described.

Figure 6:
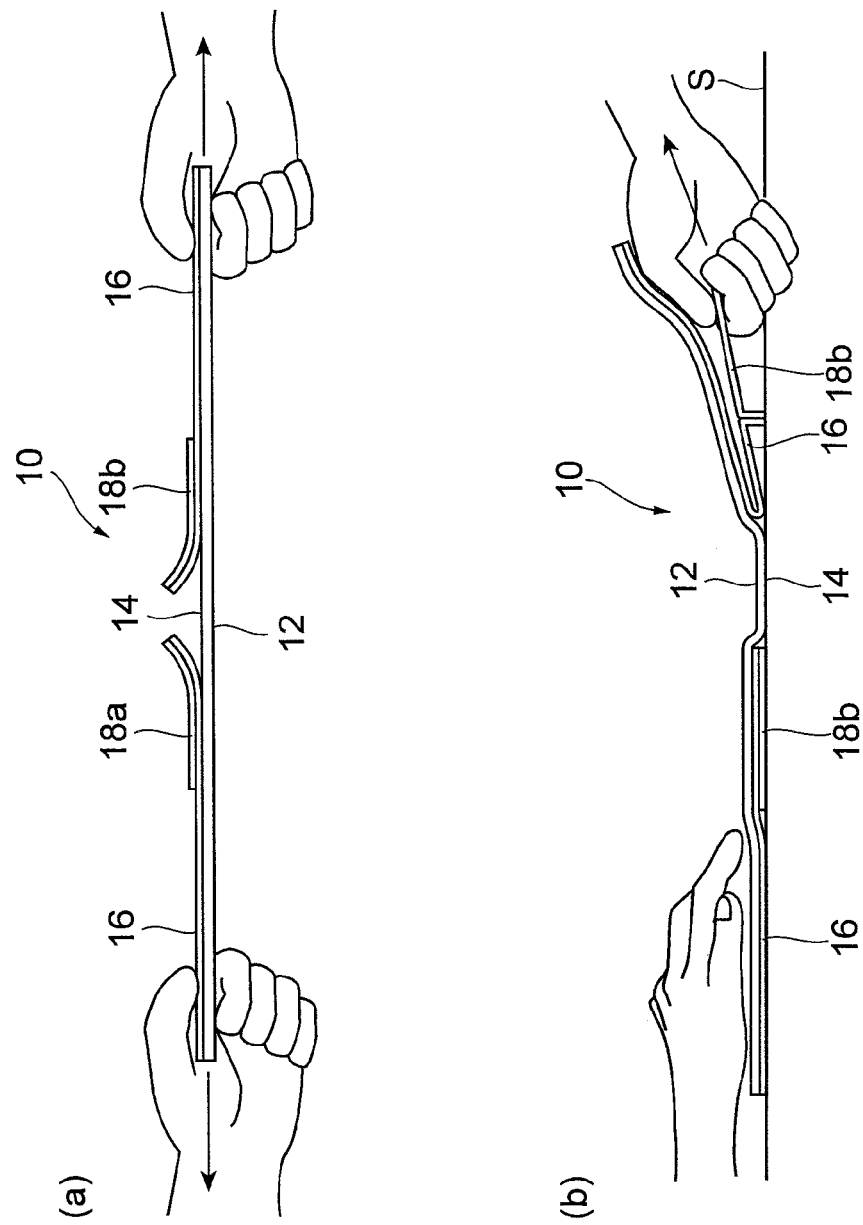
FIG. 6 are explanatory diagrams showing a procedure for applying the adhesive patch.

First, as shown in FIG. 6(*a*), both ends of the adhesive patch 10 are pinched to pull the release sheet 16 together with the support 12 to the right and left, to divide the release sheet 16 and the pinching piece forming sheet 18 to the right and left along the weakened parts 20. At this time, in the case where concavity and convexity is formed on the release sheet 16 by embossing or the like, the release sheet 16 serves as a slip stopper, which makes it easy to pull the adhesive patch 10.

Further, the fixed portions 22 include both thicknesses of the release sheet 16 and the pinching piece forming sheet 18, and the strength or the stiffness thereof is increased according to the thicknesses. Therefore, when both ends of the adhesive patch 10 are pinched to pull to the right and left, the tensile force disperses over the entire fixed portions 22. As a result, when the weakened parts 20 start breaking partially, the breakage spreads over the entire weakened parts 20 in a moment, which makes it possible to instantly divide both sheets 16 and 18.

In particular, in the case where the weakened part 20 is a perforated line, and the release sheet 16 and the pinching piece forming sheet 18 are formed of preferable materials and their thicknesses are within the preferable ranges described above, it is possible to provide a unique cutting feeling to the user because the connecting regions 20b between the perforations 20a of the perforated line are cut instantly. Further, this cutting feeling includes, not only the feeling that it is possible for a user to confirm that the release sheet 16 and the pinching piece forming sheet 18 are split into two, but also the feeling that the support 12 stretches following the instant cutting. Therefore, in the case where there is no feeling of division, but there is the feeling of stretching in a moment of pulling it, there is a possibility that the release sheet 16 of the adhesive patch 10 has been already split. That is, it is possible to offer the feeling of security to the user that the pressure-sensitive adhesive agent layer 14 of the adhesive patch 10 is protected before use, which means greater availability for the user.

In addition, in the aspect shown in FIG. 2, because the weakened parts 20 are on the non-fixed portion between the release sheet 16 and the pinching piece forming sheet 18, the weakened parts 20 are free of the influence of the fixed portions 22, i.e., heat-sealing, the adhesive, or the like. Therefore, it is possible to divide the release sheet 16 and the pinching piece forming sheet 18 while controlling cutting of the weakened parts 20.

Further, even after the release sheet 16 and the pinching piece forming sheet 18 are divided, the fixed portions 22 between both sheets 16 and 18 are not separated to maintain the fixed state. Therefore, although the shape gets some curvature, it is possible to maintain substantially the linear state or planar state. Due to such shape stability, it is possible to maintain the shape of the support 12 adhered to the fixed portions 22, which makes it possible to prevent the support 12 from wrinkling.

When the release sheet 16 and the pinching piece forming sheet 18 are divided, the pressure-sensitive adhesive agent layer 14 on the support 12 is exposed. Next, as shown in FIG. 6(b), the exposed pressure-sensitive adhesive agent layer 14 is put on the skin. Although the exposed portion of the pressure-sensitive adhesive agent layer 14 is small, the adhesive patch 10 can be provided with a temporary holding effect on the skin S. When the pinching piece forming sheet 18 is divided, the pinching pieces 18a and 18b are formed with respect to the respective release sheets 16. Therefore, by pinching and pulling the pinching pieces 18a and 18b after temporary holding of the adhesive patch 10, it is possible to apply the pressure-sensitive adhesive agent layer 14 to the skin S while releasing the divided release sheets 16 from the pressure-sensitive adhesive agent layer 14 on the support 12.

Because the free ends of the pinching pieces 18a and 18b are close to the exposed portion of the pressure-sensitive adhesive agent layer 14, and the portion at which the release sheet 16 and the pinching pieces 18a and 18b are two-layered has the thicknesses and stiffness to some extent, it is possible for a user to arrange the adhesive patch 10 at a desired position by a tactile sensation. Further, in a state in which the pinching pieces 18a and 18b are pinched, because the fingers are close to the exposed portion of the pressure-sensitive adhesive agent layer 14, it is easy to finely adjust the position of the adhesive patch 10 that dramatically improves the convenience for the user.

With respect to the adhesive patch described in the above-described Patent Literatures 1 and 2, when the adhesive patch is temporarily held on the skin, the release sheet is sandwiched between the support and the skin, which makes it difficult to release the release sheet in some cases. However, because the pinching pieces 18a and 18b are formed in the present invention, it is possible to easily release the release sheet 16 by pinching and pulling. Further, because it is possible to prevent the fingertips from touching the pressure-sensitive adhesive agent layer 14, the pressure-sensitive adhesive agent does not stick to the hands in any case.

Moreover, because not only is it possible to pinch any one of the right and left pinching pieces 18a and 18b, but it is also possible to simultaneously pinch the right and left pinching pieces 18a and 18b and also pull them, the workability for application is improved for the user.

Further, at the time of pinching and pulling the pinching pieces 18a and 18b, in the same way as that at the time of dividing the release sheets, because the stiffness of the fixed portions 22 between the release sheet 16 and the pinching pieces 18a and 18b is high, the tensile force disperses over the entire fixed portions 22, to substantially evenly act on it. When the release sheet 16 is being released from the pressure-sensitive adhesive agent layer 14 in such a state, the force substantially evenly acts on the diverging line between the release sheet 16 and the pressure-sensitive adhesive agent layer 14 (the border line with the outside of the adhered portion of the release sheet 16 and the pressure-sensitive adhesive agent layer 14). As a result, it is possible to prevent the support 12 from wrinkling, and the pressure-sensitive adhesive agent layer 14 from adhering to one another.

In this way, according to the present invention, it is possible to cleanly apply the adhesive patch 10 to the skin without making hands sticky and without wrinkling.

In addition, for the adhesive patch 10 according to the present invention, there are other usages other than the above-described method. For example, a method may be adopted in which the portions serving as the pinching pieces 18a and 18b of the pinching piece forming sheet 18 are held to pull to divide the release sheet 16 and the pinching piece forming sheet 18, and thereafter, one of the pinching pieces 18a and 18b is pinched to release the release sheet 16 on the side thereof, to expose the half of the pressure-sensitive adhesive agent layer 14 on the support 12, and thereafter, it is applied to the skin. In this case, because the pinching pieces 18a and 18b are symmetrically formed, it is possible for a user to freely select one of the pinching pieces 18a and 18b which is easy to be pinched, which is convenient.

As one aspect of the present invention for preferably exerting the above-described function effects, a poultice may be cited. The poultice is formed such that the support 12 is a non-woven fabric, and the pressure-sensitive adhesive agent layer 14 is aqueous gel. In the case where the pressure-sensitive adhesive agent layer 14 is aqueous gel, because it has a sufficient thickness and a sufficient weight, moderate releasing strength is provided thereto, and the release sheet 16 is not released too easily in any case. Therefore, because there is no need to provide anti-releasing means such as a wound dressing described in Patent Literature 5, manufacturing is easy and the cost is low.

[Adhesive Patch Manufacturing Method and Adhesive Patch Manufacturing Apparatus According to the Present Invention]

Figure 7:
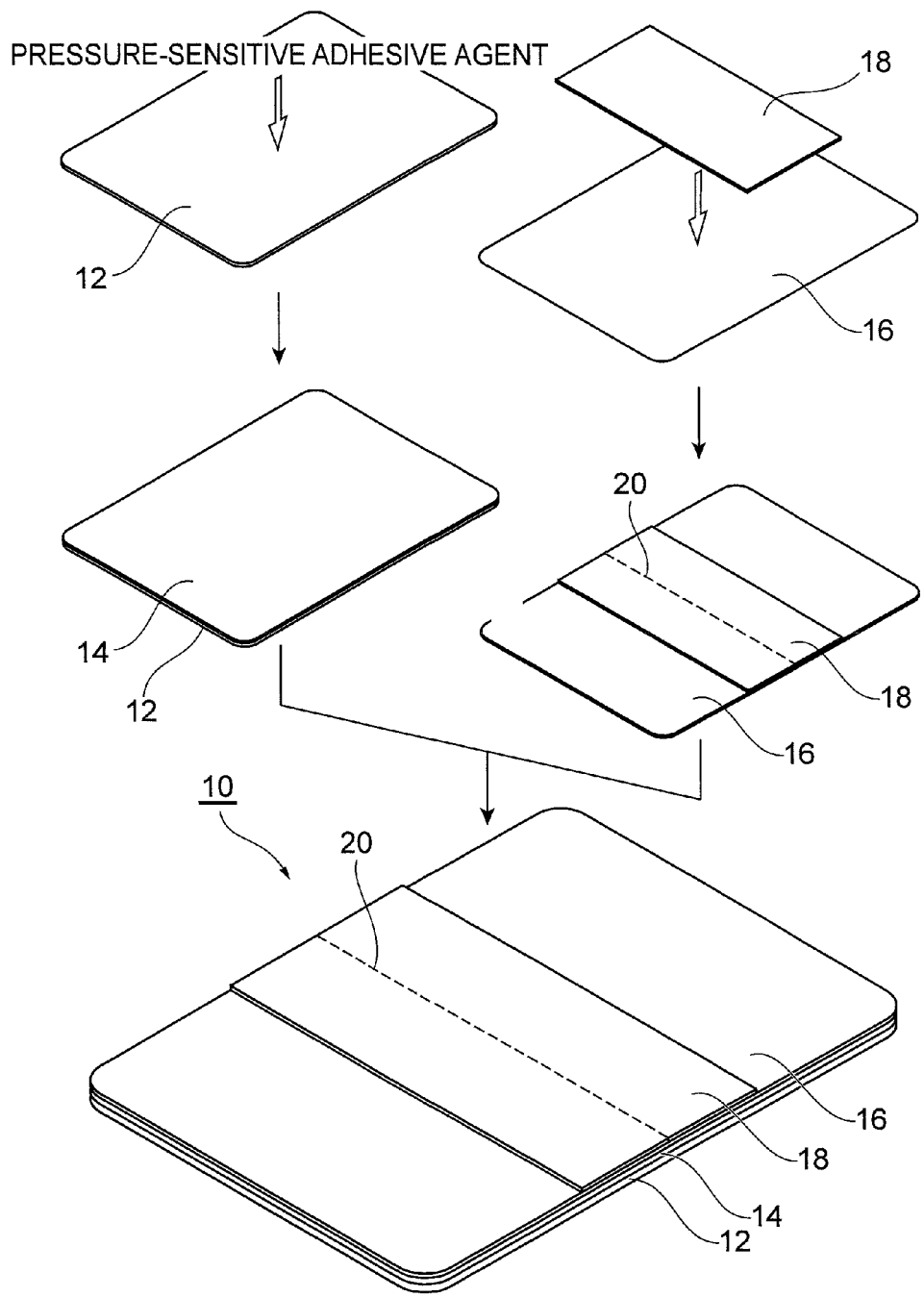
FIG. 7 is an explanatory diagram showing a basic method for manufacturing the adhesive patch of FIG. 1.

A method according to the present invention for manufacturing the adhesive patch 10 having an excellent effect as described above is basically performed in processes shown in FIG. 7. That is, first, the support 12 is prepared, and the pressure-sensitive adhesive agent layer 14 is formed on one surface thereof. Further, the pinching piece forming sheet 18 is fixed to the release sheet 16, and thereafter, the weakened parts 20 such as perforated lines are formed. Then, the release sheet 16 having the pinching piece forming sheet 18 is adhered to the pressure-sensitive adhesive agent layer 14 on the support 12. As a fixing method, there is a method using an adhesive, a heat-sealing method, or the like as described above.

The method shown in FIG. 7 is a type in which adhesive patches are manufactured one by one. However, there is a method for continuously manufacturing the adhesive patches 10 as well. That is, the continuous adhesive patch manufacturing method includes a first step of unwinding a first continuous web which will be the support 12 from a first original roll, to form a pressure-sensitive adhesive agent layer 14 on the first continuous web, a second step of unwinding a second continuous web which will be the release sheet 16 from a second original roll, unwinding a third continuous web which will be the pinching piece forming sheet 18 from a third original roll, and superposing the third continuous web on the second continuous web to fix both sheets, a third step of forming a weakened part in the second continuous web and the third continuous web which are fixed, a fourth step of releasably adhering the second continuous web to which the third continuous web is fixed, that has been obtained in the third step, to the pressure-sensitive adhesive agent layer 14 on the first continuous web, that has been obtained in the first step, so as to form a laminated body, and a fifth step of cutting out the laminated body obtained in the fourth step to a predetermined size, so as to form the adhesive patch 10.

Figure 8:
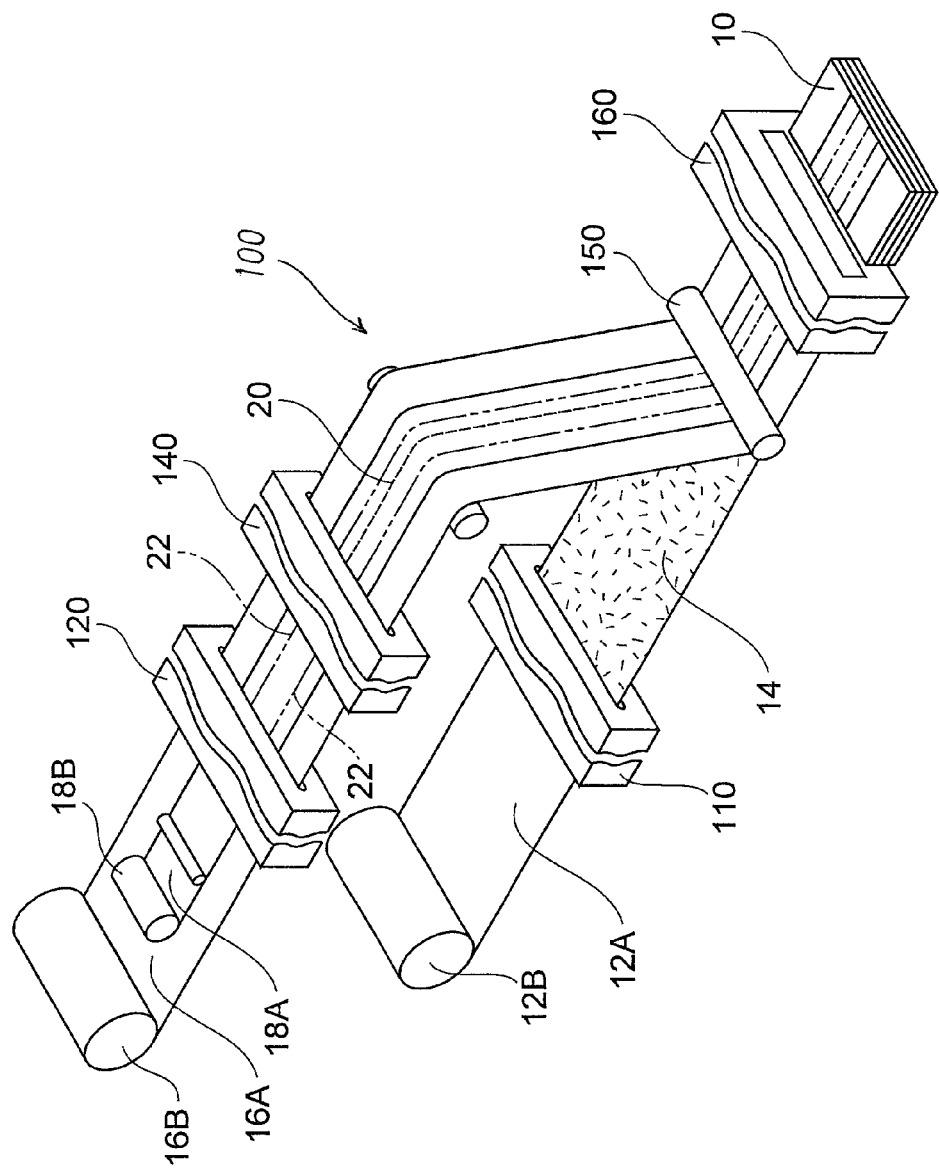
FIG. 8 is an explanatory diagram showing a manufacturing method and a manufacturing apparatus in the case where the adhesive patch of FIG. 1 is continuously manufactured.

In order to preferably implement this method, it is effective to use an adhesive patch manufacturing apparatus 100 according to the present invention as schematically shown in FIG. 8. The illustrated apparatus 100 is composed of a spreading and adhering unit 110 that spreads and adheres a pressure-sensitive adhesive agent on a first continuous web 12A which will be the support 12, to form the pressure-sensitive adhesive agent layer 14, a fixing unit 120 that fixes a third continuous web 18A which will be the pinching piece forming sheet 18, to a second continuous web 16A which will be the release sheet 16, a weakened part forming unit 140 that forms the weakened parts 20 in the second and third continuous webs 16A and 18A passing through the fixing unit 120, a laminated body forming unit 150 which adheres the second and third continuous webs 16A and 18A passing through the weakened part forming unit 140, on the pressure-sensitive adhesive agent layer 14 of the first continuous web 12A passing through the spreading and adhering unit 110, so as to form a laminated body 24, and a cutting unit 160 that cuts out the laminated body 24 of the first to third continuous webs 12A, 16A, and 18A passing through the laminated body forming unit 150, so as to be the adhesive patch 10 as a finished product.

The first continuous web 12A is unwound from a rolled first original roll 12B, which is rotatably held on the upstream side of the spreading and adhering unit 110, to be fed to the spreading and adhering unit 110. The spreading and adhering unit 110 is a conventionally-known configuration, that spreads and adheres a pressure-sensitive adhesive agent on the top surface of the first continuous web 12A, to form the pressure-sensitive adhesive agent layer 14.

On the other hand, the second continuous web 16A and the third continuous web 18A are respectively unwound from a rolled second original roll 16B and a rolled third original roll 18B, which are rotatably held on the upstream side of the fixing unit 120, and both continuous webs 16A and 18A in a superposed state are fed to the fixing unit 120.

Fixing of both continuous webs 16A and 18A at the fixing unit 120 may be carried out by use of an adhesive. However, the equipment may tend to become complex, and therefore, it is effective to carry out the fixing by use of a heat-sealing device. Further, as a heat-sealing device, there is a roller type having a pair of heating seal rollers. However, a press type is preferable for reliable heat-sealing.

Figure 9:
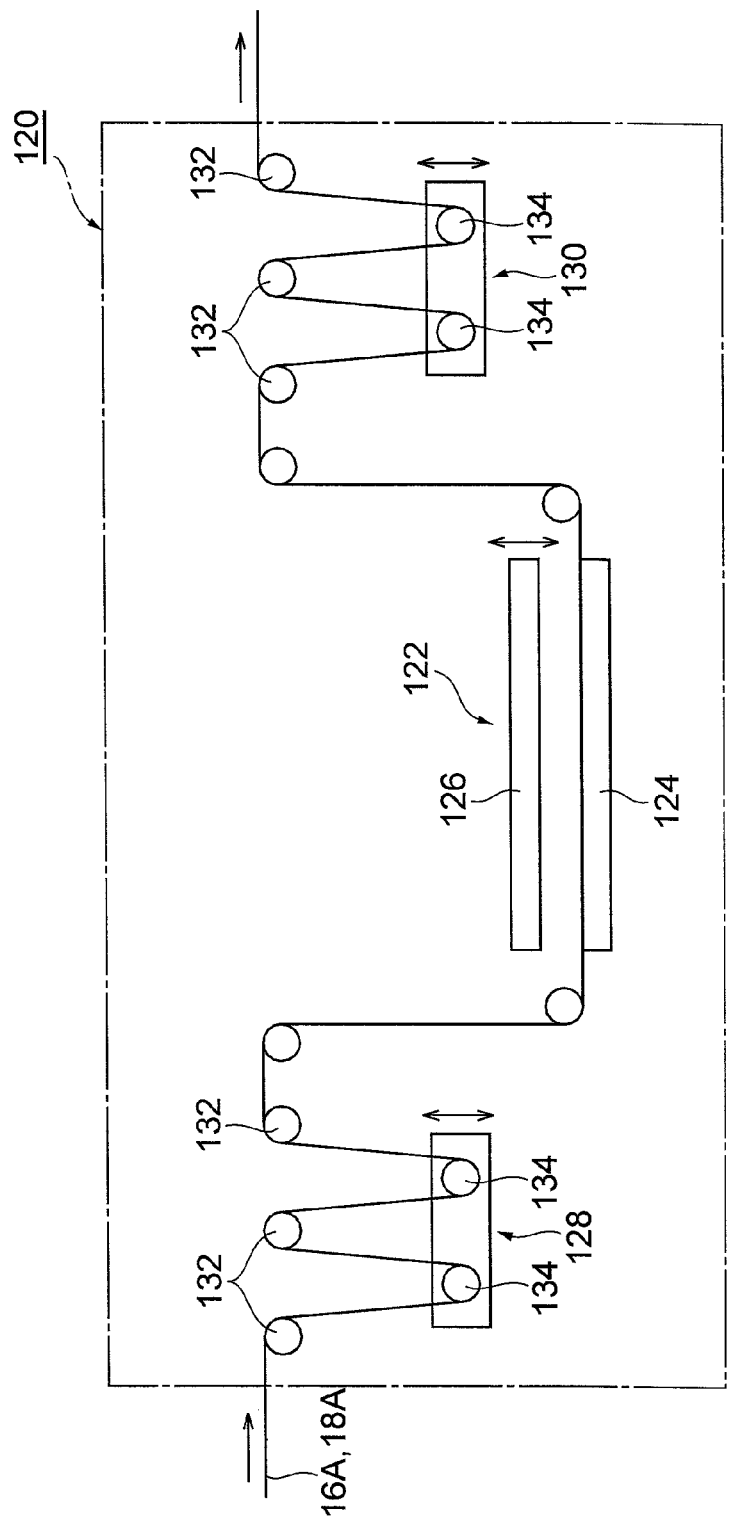
FIG. 9 is a side view schematically showing a concrete configuration of a fixing unit in the manufacturing apparatus of FIG. 8.

FIG. 9 is a side view schematically showing the fixing unit 120 having a press type heat-sealing device 122. The illustrated heat-sealing device 122 includes a fixed seal bar 124 and a movable seal bar 126 arranged so as to be vertically movable above the fixed seal bar 124. When the movable seal bar 126 is moved down, the fixed seal bar 124 and the movable seal bar 126 contact each other. Further, because both or either of the fixed seal bar 124 and the movable seal bar 126 are heated up to a temperature required for heat-sealing, when the second and third continuous webs 16A and 18A are fed between the fixed seal bar 124 and the movable seal bar 126 in a heated state, and both continuous webs 16A and 18A are pressed between these seal bars 124 and 126, both continuous webs 16A and 18A are heat-sealed at the portion on which the seal bars 124 and 126 contact each other. It is possible to adjust the fixing strength of the fixed portion 22 by the heat-sealing by appropriately changing the parameters such as a pressing time, a pressing pressure and heating temperature. In addition, even in the case where concavity and convexity is formed on the second continuous web 16A by embossing or the like, by use of the press type heat-sealing device 122, it is possible to ensure a sufficient pressing time and pressing pressure. Therefore, there is the advantage that it is possible to reliably carry out heat-sealing of the second continuous web 16A and the third continuous web 18A. In addition, a flat plate, i.e., a so-called anvil, may be used in place of the fixed seal bar 124.

In addition, in the embodiment shown in FIG. 8, two pairs of the fixed and movable seal bars 124 and 126 are provided in parallel to the feeding direction of the continuous webs 16A and 18A, thereby forming the two fixed portions 22.

During the process of heat-sealing, it is necessary to stop the feeding of the second and third continuous webs 16A and 18A with respect to the respective seal bars 124 and 126 at the portion of the heat-sealing device 122. In the case where the feeding of the second and third continuous webs 16A and 18A is intermittently carried out, because the first continuous web 12A is continuously fed, it is difficult to superpose the first continuous web 12A and the second and third continuous webs 16A and 18A in the laminated body forming unit 150, and therefore, it is necessary to intermittently carry out feeding of the first continuous web 12A as well. This leads to a decrease in efficiency of manufacture.

Then, a first accumulation device 128 and a second accumulation device 130 which are capable of accumulating or retaining the second and third continuous webs 16A and 18A, are respectively provided on the upstream side and the downstream side of the heat-sealing device 122 in the fixing unit 120 shown in FIG. 9, so as to continuously carry out feeding of the second and third continuous webs 16A and 18A.

As the accumulation devices 128 and 130, various modes may be conceived of, and a mechanism as shown in FIG. 9 may be used. The illustrated mechanism is composed of a plurality of guide rollers 132 rotatably attached to certain places, and movable rollers 134 disposed between the adjacent guide rollers 132. The movable rollers 134 are configured to be able to approach and move away from the guide rollers 132. Further, the movable rollers 134 are configured to move away from the guide rollers 132 in an unloaded state by springs or the like. In such a mechanism, the second and third continuous webs 16A and 18A are brought into a state in which the continuous webs are alternately wound around the guide rollers 132 and the movable rollers 134, and when tensile force higher than a predetermined value acts on the continuous webs 16A and 18A, the movable rollers 134 approach the guide rollers 132, and in contrast, when tensile force becomes lower than the predetermined value, the movable rollers 134 move away from the guide rollers 132.

In the case where the accumulation devices 128 and 130 with such a mechanism are provided on the upstream side and the downstream side of the heat-sealing device 122, this operates as follows.

First, in a state in which heat-sealing is not being carried out, the second and third continuous webs 16A and 18A with predetermined tensile force are guided by the guide rollers 132 and the movable rollers 134, to continuously travel.

Even during the process of heat-sealing of the second and third continuous webs 16A and 18A by the heat-sealing device 122, continuously, the second and third continuous webs 16A and 18A are fed to the fixing unit 120 from the original rolls 16B and 18B. However, because the tensile force of the second and third continuous webs 16A and 18A is reduced in the first accumulation device 128 on the upstream side, the movable rollers 134 move away from the guide rollers 132 so as to extend the sheet path length in the first accumulation device 128. Because the second and third continuous webs 16A and 18A of this extended length are accumulated in the first accumulation device 128, there is no need to stop unwinding the continuous webs 16A and 18A from the original materials 16B and 18B.

On the other hand, at the time of heat-sealing when the second and third continuous webs 16A and 18A are directly fed to the laminated body forming unit 150 on the downstream side of the heat-sealing device 122, because the tensile force of the second and third continuous webs 16A and 18A is reduced in the second accumulation device 130 on the downstream side, the movable rollers 134 approach the guide rollers 132. As a result, the second and third continuous webs 16A and 18A accumulated in the second accumulation device 130 are fed out.

Therefore, even when the feeding of the second and third continuous webs 16A and 18A is intermittently carried out by the heat-sealing device 122, feeding into the fixing unit 120 and feeding out of the fixing unit 120 are continuously carried out by the presence of the accumulation devices 128 and 130, and therefore, it is possible to continuously carry out superposition of the second and third continuous webs 16A and 18A and the first continuous web 12A uninterruptedly.

The second and third continuous webs 16A and 18A two-layered in the fixing unit 120 are fed to the weakened part forming unit 140, to form the weakened parts 20. As the weakened part forming unit 140, a conventionally well-known device may be used. For example, a device composed of a roller having a blade for forming a perforated line, a groove, or the like, a device that forms a perforated line, a groove, or a fragile part by irradiation of a laser beam, or the like may be cited. In addition, in the embodiment shown in FIG. 8, the weakened parts 20 are formed in the center between the two fixed portions 22 formed in advance.

The second and third continuous webs 16A and 18A in which the weakened parts 20 such as perforated lines are formed at the weakened part forming unit 140 are thereafter superposed on the pressure-sensitive adhesive agent layer 14 of the first continuous web 12A at the laminated body forming unit 150, to become the laminated body 24, and is fed to the cutting unit 160. The laminated body 24 is cut out in a predetermined size and timing at the cutting unit 160, to complete the desired adhesive patch 10.

In the manufacturing method and the manufacturing apparatus 100 as described above, because folding processing is not required for the second and third continuous webs 16A and 18A which will be the release sheet 16 and the pinching piece forming sheet 18, and it is possible to continuously carry out fixing of the second continuous web 16A and the third continuous web 18A and formation of the weakened parts 20 along the sheet feeding direction, and therefore, it is possible to efficiently carry out the manufacture.

In particular, in the case where the fixing of the second continuous web 16A and the third continuous web 18A is carried out by use of the press type heat-sealing device 122, even when concavity and convexity such as embossment is formed on the second continuous web 16A, it is possible to reliably fix the second continuous web 16A to the third continuous web 18A. On the other hand, the present invention corresponds to the intermittent feeding in the case where the press type heat-sealing device 122 is used, by the accumulation devices 128 and 130, thereby it is possible to exercise the effect that it is possible to continuously carry out superposition of the first continuous web 12A with the second and third continuous webs 16A and 18A, and the final cutting thereof.

Modified Embodiments and the Like

The preferred embodiments of the present invention have been described in detail above. However, it is a matter of course that the present invention is not limited to the above-described embodiments.

For example, in the above-described embodiments, the support 12 has stretching properties. However, in the case where there is no need to divide the release sheet 16 by pulling the adhesive patch 10 to the right and left, the stretching properties of the support 12 are not required.

Further, in the embodiment shown in FIGS. 1 to 3, the right and left fixed portions 22 are spaced from the weakened parts 20. However, because the fixed portions 22 are formed at positions relatively close to the weakened parts 20, it is difficult to pinch the inner portions of the pinching piece forming sheet 18 (the portions on the opposite side of the pinching pieces 18a and 18b) after dividing the sheet. Then, as shown in FIG. 10, an aspect in which the right and left fixed portions 22 are formed at positions relatively separated away, for example, by approximately 15 to 25 mm from the weakened parts 20, may be conceived of.

Figure 10:
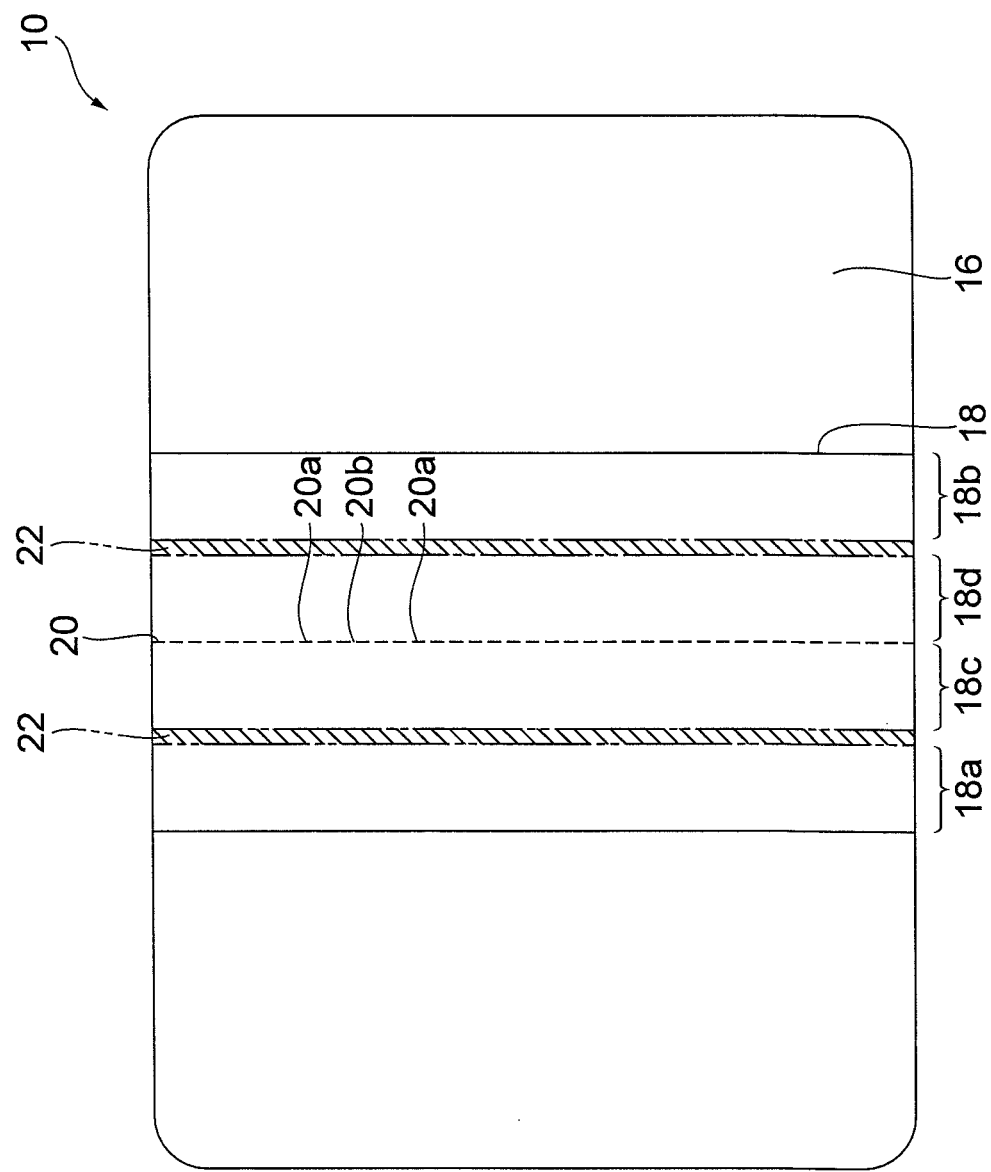
FIG. 10 is a plan view showing a modified embodiment of an adhesive patch according to the present invention.
Figure 11:
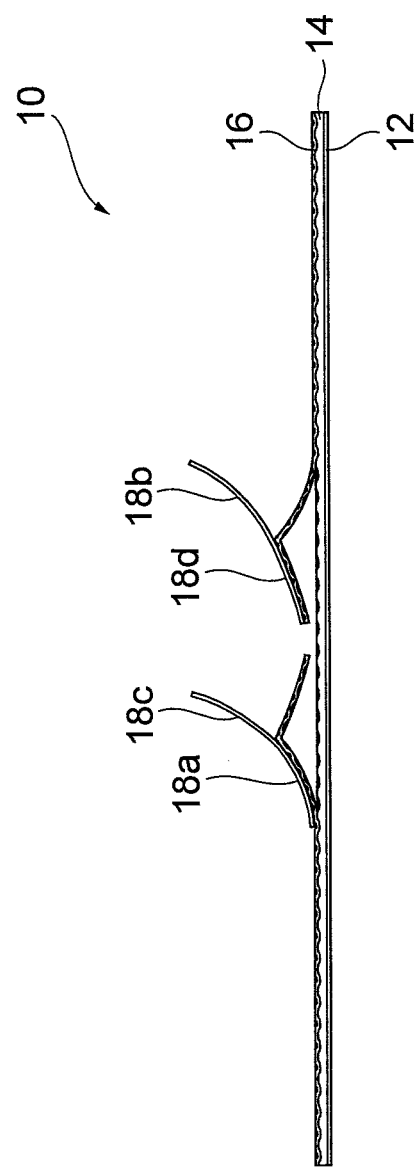
FIG. 11 is a side view showing the adhesive patch of FIG. 10 that is a diagram showing an example of a mode of use after dividing a release sheet and a pinching piece forming sheet.

In the embodiment as shown in FIG. 10, after the release sheet 16 and the pinching piece forming sheet 18 are divided along the weakened parts 20, not only the outer portions 18a and 18b, but also inner portions 18c and 18d function as pinching pieces. Thereby, it is possible to provide various usages according to the convenience of a user. For example, as shown in FIG. 11, it is possible to pinch the inner pinching piece 18c on the left side and the outer pinching piece 18b on the right side, to release the release sheet 16.

Figure 12:
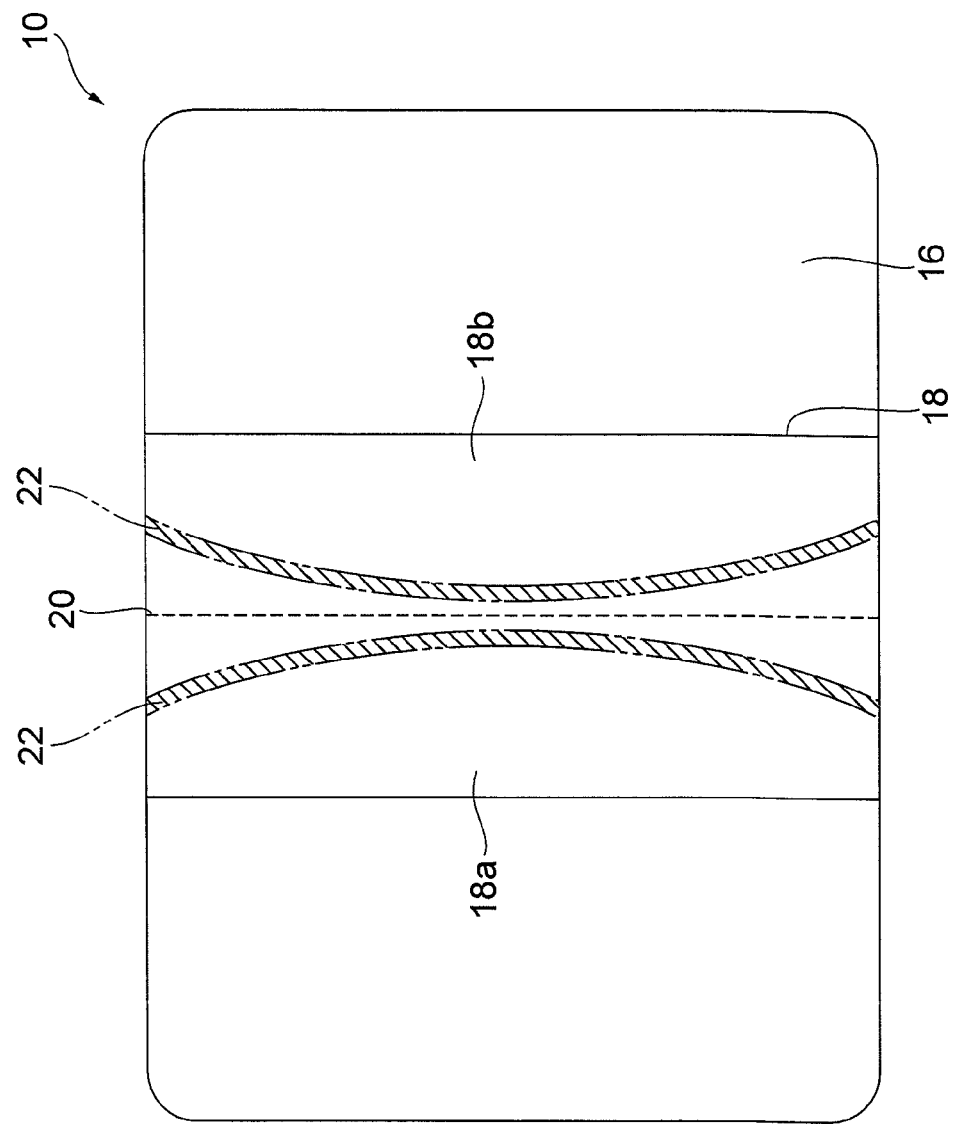
FIG. 12 is a plan view showing another modified embodiment of the adhesive patch according to the present invention.

Further, the shape of the fixed portions 22 may be not only the linear shape as that in FIG. 2, but also another shape, for example, a curved line shape as shown in FIG. 12. In a case of the non-linear shaped fixed portions 22, in particular, fixing by a heat-sealing method is easily carried out, which is favorable. In a case of the shape shown in FIG. 12, after the pinching piece forming sheet 18 is cut off along the weakened parts 20, when the pinching pieces 18a and 18b are pulled to the right and left, it is possible to sterically curve it so as to float the exposed surface (medicinal agent surface) of the pressure-sensitive adhesive agent layer 14 of the adhesive patch 10, which makes it possible to easily apply the adhesive patch 10 without bringing about wrinkles on the body surface to be applied. Further, because the space between the two fixed portions 22 is narrowed in the central portion of the adhesive patch 10, at the time of pulling the pinching pieces 18a and 18b to the right and left, the tensile force is concentrated on the weakened parts 20 located in the central portion of the adhesive patch 10, which makes it easy to divide the release sheet 16 and the pinching piece forming sheet 18. Moreover, the space between the two fixed portions 22 is widened on the long sides of the adhesive patch 10, a usage by pinching these portions as shown in FIG. 11 may be adopted.

In addition, in contrast to the embodiment in FIGS. 1 to 3, a state in which the outer portions 18a and 18b are made smaller or completely removed, and only the inner portions 18c and 18d are served as pinching pieces is within the scope of the present invention.

Figure 13:
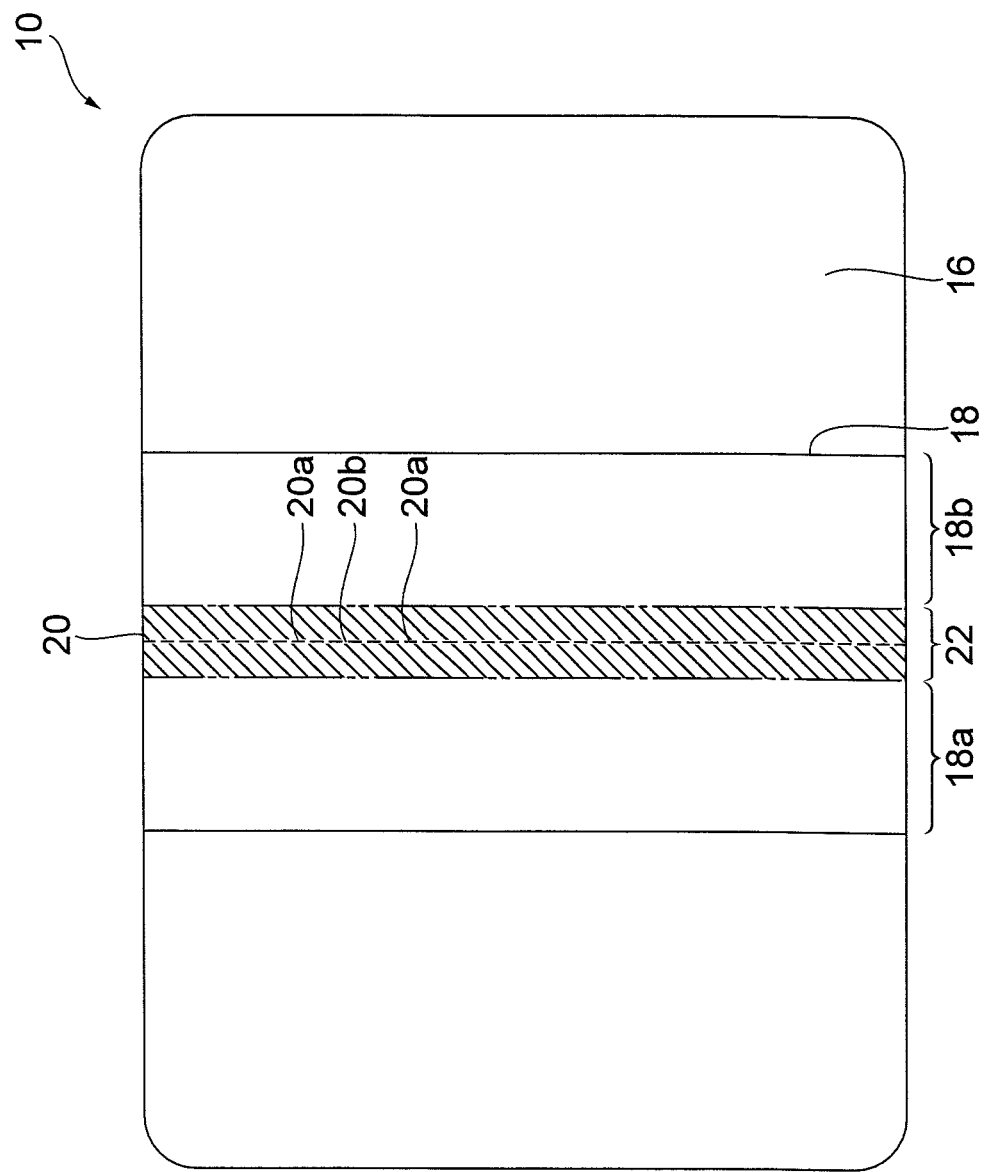
FIG. 13 is a plan view showing yet another modified embodiment of the adhesive patch according to the present invention.

Furthermore, there is no need to form the fixed portions 22 at two places at the right and left. As shown in FIG. 13, the release sheet 16 and the pinching piece forming sheet 18 may be fixed at one place in substantially the central portion, and the weakened parts 20 may be formed on the one fixed portion 22. In this case, there is only a pair of the fixed seal bar 124 and the movable seal bar 126 in the press type heat-sealing device 122.

Figure 14:
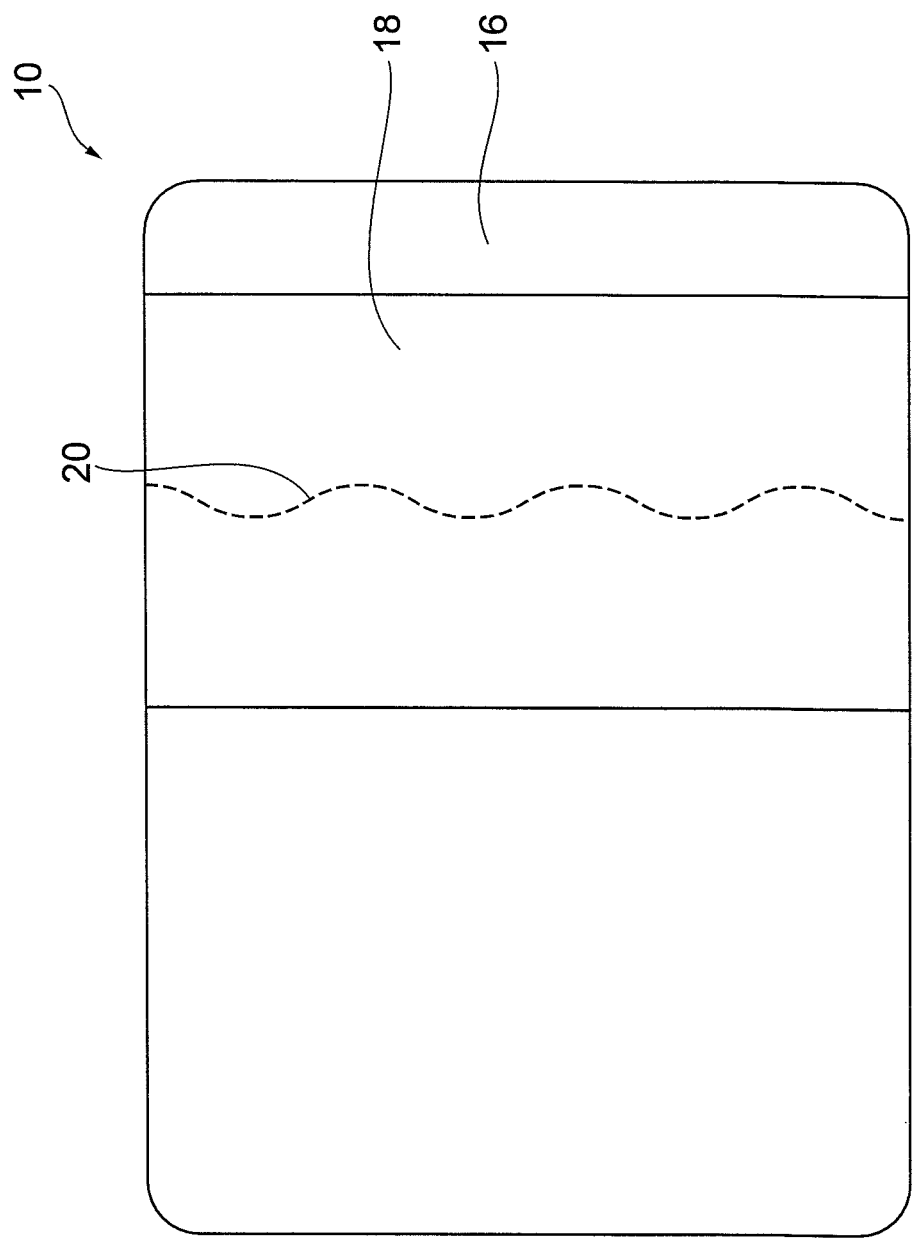
FIG. 14 is a plan view showing yet another modified embodiment of the adhesive patch according to the present invention.

Further, as shown in FIG. 14, the pinching piece forming sheet 18 may be fixed at a position off-set from the central portion of the release sheet 16.

Moreover, the weakened part 20 is not limited to a straight line, and may be formed into a wave shape or a saw-tooth shape as shown in FIG. 14. In this case, the shape of the fixed portions 22 may be formed into a wave shape or a saw-tooth shape so as to correspond to the shape of the weakened part 20.

Figure 15:
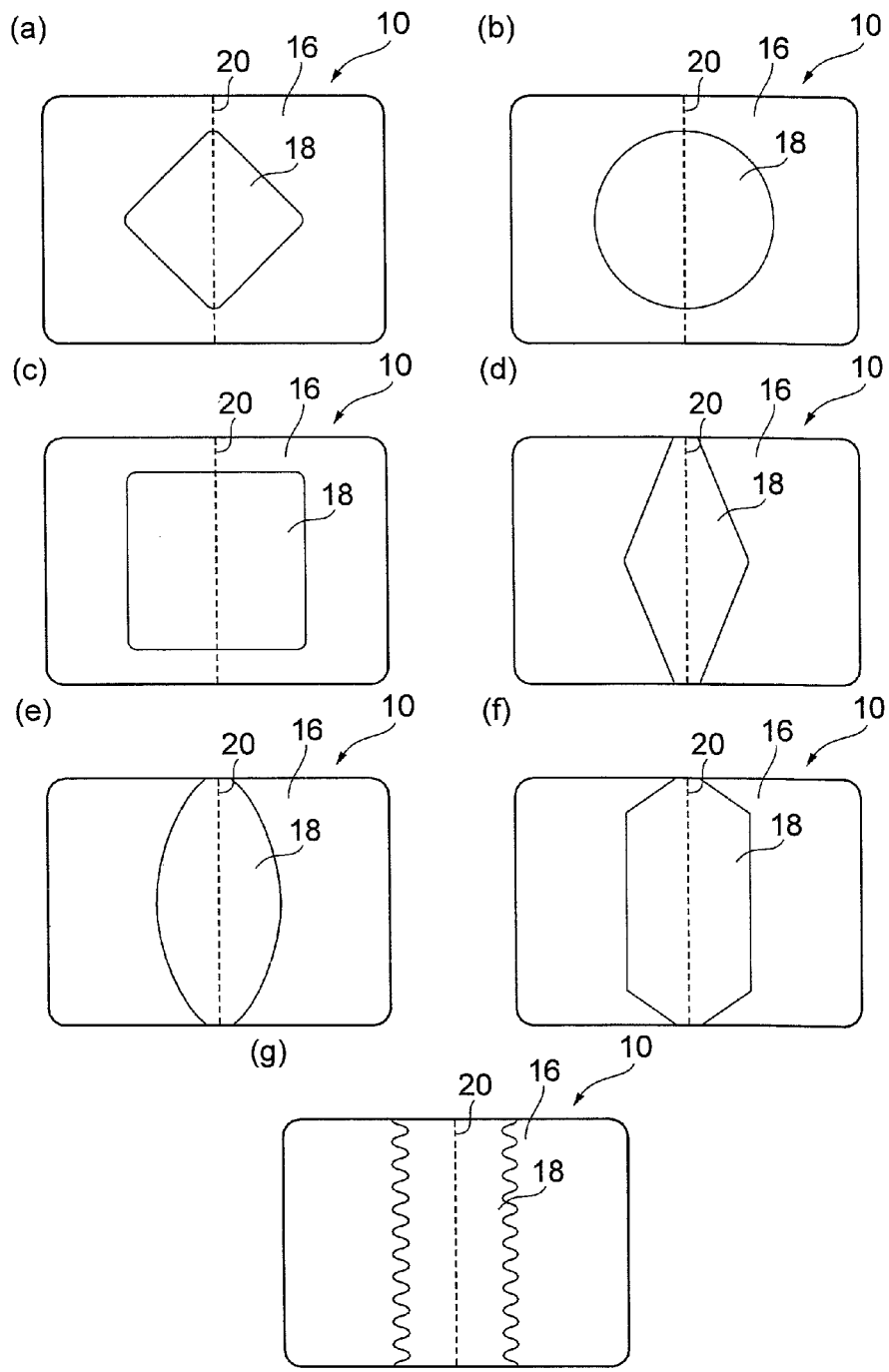
FIGS. 15(*a*) to 15(*g*) are respectively plan views showing various modified embodiments of the adhesive patches according to the present invention.

Further, the pinching piece forming sheet 18 may be formed into a shape other than the rectangular shape, for example, various shapes as shown in FIGS. 15(*a*) to 15(*g*). Further, a mode in which the pinching piece forming sheet 18 does not cross over the entire adhesive patch 10 as shown in FIGS. 15(*a*) to 15(*c*) may be adopted. In addition, the fixed portions are not shown in FIG. 15.

It may be easily understood that the adhesive patch manufacturing method and apparatus of the present invention are applicable to various adhesive patches according to modified embodiments as described above. In the case where the pinching piece forming sheet 18 does not cross over the entire adhesive patch 10 as in FIGS. 15(*a*) to 15(*c*), the adhesive patch manufacturing apparatus shown in FIG. 8 is not applicable directly. However, for example, by adopting the configuration in which the pinching piece forming sheet is arranged in an appropriate timing on the second continuous web immediately before entering into the heat-sealing device in the fixing unit, it is possible to manufacture the adhesive patches of FIGS. 15(*a*) to 15(*c*).

REFERENCE SIGNS LIST

10 . . . Adhesive patch, 12 . . . Support, 12A . . . First continuous web which will be a support, 14 . . . Pressure-sensitive adhesive agent layer, 16 . . . Release sheet, 16A . . . Second continuous web which will be a release sheet, 18 . . . Pinching piece forming sheet, 18*a*, 18*b*, 18*c*, 18*d* . . . Pinching pieces, 18A . . . Third continuous web which will be a pinching piece forming sheet, 20 . . . Weakened part, 22 . . . Fixed portion, 24 . . . Laminated body, 100 . . . Adhesive patch manufacturing apparatus, 110 . . . Spreading and adhering unit, 120 . . . Fixing unit, 122 . . . Heat-sealing device, 124 . . . Fixed seal bar, 126 . . . Movable seal bar, 128 . . . First accumulation apparatus, 130 . . . Second accumulation apparatus, 132 . . . Guide roller, 134 . . . Movable roller, 140 . . . Weakened part forming unit, 150 . . . Laminated body forming unit, 160 . . . Cutting unit.

The invention claimed is:

1. A method for continuously manufacturing adhesive patches, the adhesive patches each including a support having a pressure-sensitive adhesive agent layer on one surface of the support, and a release sheet releasably attached thereto, the release sheet including a weakened part for easily dividing the release sheet into two parts, and a pinching piece forming sheet fixed to the release sheet and positioned on and covering the weakened part of the release sheet, the pinching piece forming sheet having non-fixed pinching pieces, and a weakened part formed at a position corresponding to the weakened part of the release sheet, the method comprising:
a first step of forming the support with the pressure-sensitive adhesive agent layer, comprising:
unwinding a first continuous web of a support material having stretching properties from a first original roll, and
adhering a pressure-sensitive adhesive agent on the support material;
a second step of continuously fixing pinching piece forming sheet material on release sheet material, comprising:
unwinding a second continuous web of the release sheet material from a second original roll,
unwinding a third continuous web of the pinching piece sheet forming material from a third original roll,
temporarily accumulating the release sheet material and the pinching piece forming sheet material in a first accumulation device (128) located upstream from a press type heat-sealing device, wherein the first accumulation device comprises a plurality of guide rollers (132) and a set of movable rollers (134),
continuously feeding the release sheet material and the pinching piece forming sheet material to the press type heat-sealing device and superposing and fixing two portions of the pinching piece forming sheet material on the release sheet material by heat-sealing, wherein the two fixed portions are capable of dispersing a tensile force applied to the adhesive patch, and temporarily accumulating the fixed release sheet material and the pinching piece forming sheet material in a second accumulation device (130) located downstream from the press type heat-sealing device and continuously feeding the fixed release sheet and pinching piece forming sheet materials to the downstream side, wherein the second accumulation device comprises a second plurality of guide rollers (132) and a second set of movable rollers (134);
a third step of continuously forming the weakened parts (20) in the fixed release sheet and pinching piece forming sheet materials, comprising:
forming a weakened part in the release sheet material and a corresponding weakened part (22) in the pinching piece forming sheet material, wherein the two fixed portions are positioned on a right side and a left side of the weakened parts, wherein the weakened parts are divisible when the tensile force is applied to the adhesive patch;
a fourth step of continuously forming a laminated body, comprising:
releasably adhering the pinching piece forming sheet material fixed on the release sheet material to the support material with the pressure-sensitive adhesive agent on the support material; and
a fifth step of forming the adhesive patch, comprising:
cutting out the laminated body to a predetermined size.

2. The method according to claim 1, wherein the first continuous web of the support material is selected from the group consisting of a woven fabric, a knit fabric, a nonwoven paper, and a film.

3. The method according to claim 1, wherein the first continuous web of the support material has a 50% modulus of 0.5 to 10 N/50 mm in a crosswise direction and a transverse direction.

* * * * *